US010226486B2

(12) United States Patent
Cho et al.

(10) Patent No.: US 10,226,486 B2
(45) Date of Patent: Mar. 12, 2019

(54) METHOD FOR PREPARATION OF INDUCED DOPAMINERGIC PROGENITORS USING DIRECT REPROGRAMMING

(71) Applicant: KOREA RESEARCH INSTITUTE OF BIOSCIENCE AND BIOTECHNOLOGY, Daejeon (KR)

(72) Inventors: Yee Sook Cho, Daejeon (KR); Jang Hwan Kim, Daejeon (KR); Han Seop Kim, Daejeon (KR)

(73) Assignee: KOREA RESEARCH INSTITUTE OF BIOSCIENCE AND BIOTECHNOLOGY (KR)

( * ) Notice: Subject to any disclaimer, the term of this patent is extended or adjusted under 35 U.S.C. 154(b) by 176 days.

(21) Appl. No.: 14/908,817

(22) PCT Filed: Oct. 4, 2013

(86) PCT No.: PCT/KR2013/008888
§ 371 (c)(1),
(2) Date: May 11, 2016

(87) PCT Pub. No.: WO2015/016420
PCT Pub. Date: Feb. 5, 2015

(65) Prior Publication Data
US 2016/0256495 A1  Sep. 8, 2016

(30) Foreign Application Priority Data
Jul. 31, 2013  (KR) ........................ 10-2013-0091179

(51) Int. Cl.
*C12N 5/00* (2006.01)
*A61K 35/30* (2015.01)
*C12N 5/0797* (2010.01)
*A61K 49/00* (2006.01)
*G01N 33/50* (2006.01)

(52) U.S. Cl.
CPC .......... *A61K 35/30* (2013.01); *A61K 49/0004* (2013.01); *C12N 5/0623* (2013.01); *G01N 33/5058* (2013.01); *G01N 33/5073* (2013.01); *C12N 2501/119* (2013.01); *C12N 2501/41* (2013.01); *C12N 2501/415* (2013.01); *C12N 2501/727* (2013.01); *C12N 2506/02* (2013.01); *C12N 2506/1307* (2013.01); *C12N 2510/00* (2013.01); *G01N 2800/2835* (2013.01)

(58) Field of Classification Search
CPC .............................. C12N 5/0623; A61K 35/30
See application file for complete search history.

(56) References Cited

U.S. PATENT DOCUMENTS

| 2005/0196864 A1* | 9/2005 | Goldman | C12N 5/0622 435/456 |
| 2010/0021437 A1* | 1/2010 | Isacson | C12N 5/0618 424/93.7 |
| 2014/0141451 A1* | 5/2014 | Nichols | C07K 16/44 435/7.4 |

OTHER PUBLICATIONS

Takagi et al. Journal of Clinical Investigation 115(1):102-109, 2005.*
Wernig et al. Nautre 448:318-325, 2007 (Year: 2007).*
Deleidi et al. (May 2011) "Oct4-induced reprogramming is required for adult brain neural stem cell differentiation into midbrain dopaminergic neurons," PLoS One. 6(5):e19926. pp. 1-13.
Hu et al. (2010) "Neural differentiation of human induced pluripotent stem cells follows developmental principles but with variable potency," Proc. Natl. Acad. Sci. USA. 107(9):4335-4340.
Jiang et al. (2003) "Neuroectodermal differentiation from mouse multipotent adult progenitor cells," Proc. Natl. Acad. Sci. USA. 100(Suppl 1):11854-11860.
Kim et al. (May 10, 2011) "Direct reprogramming of mouse fibroblasts to neural progenitors," Proc. Natl. Acad. Sci. USA. 108(19):7838-7843.
Wakayama et al. (2001) "Differentiation of embryonic stem cell lines generated from adult somatic cells by nuclear transfer," Science. 292:740-743.
Wernig et al. (2008) "Neurons derived from reprogrammed fibroblasts functionally integrate into the fetal brain and improve symptoms of rats with Parkinson's disease," Proc. Natl. Acad. Sci. USA. 105(15):5856-5861.
International Search Report and Written Opinion as it relates to International Application No. PCT/KR2013/008888 dated Apr. 25, 2014.
Liu et al. (Nov. 22, 2011) "Direct reprogramming of human fibroblasts into dopaminergic neuron-like cells," Cell Res. 22:321-332.
Sanchez-Danes (Jan. 2012) "Efficient generation of A9 midbrain dopaminergic neurons by lentiviral delivery of LMX1A in human embryonic stem cells and induced pluripotent stem cells. Human Gene Therapy," Human Gene Therapy. 23:56-69.

* cited by examiner

*Primary Examiner* — Marcia S Noble
(74) *Attorney, Agent, or Firm* — Lathrop Gage LLP; Andrew T. Wilkins; Michael J. Spellberg

(57) ABSTRACT

The present invention relates to a method for preparing induced dopaminergic neuronal progenitors (iDPs) comprising inducing an expression of Oct4, Sox2, Klf4, and c-Myc genes in adult cells and direct reprogramming of the adult cells to the iDPs by treating the cells with sonic hedgehog (SHH) and fibroblast growth factor 8 (FGF8); and a cell therapy product and a composition for treating or preventing Parkinson's Disease (PD) which comprises the iDPs as active ingredients. In addition to this, the present invention relates to a method for preparing midbrain dopaminergic neurons comprising isolating NSC-like colony by culturing the iDPs, dissociating the isolated NSC-like colony, and culturing the cells on the neural cell differentiation medium. Further, the present invention relates to a method for treating PD or a method for screening medicine for preventing or treating PD using the cells of the present invention. The progenitors prepared by the method for preparing the iDPs of the present invention can be widely used in the known art since the neuronal progenitors have significantly higher efficiency in differentiating to the dopaminergic neurons compared to conventional methods and lack side effects such as immunogenicity and ethical issues because patients' own somatic cells can be used.

9 Claims, 16 Drawing Sheets

Specification includes a Sequence Listing.

TH/TUJ1

METHOD FOR PREPARATION OF INDUCED DOPAMINERGIC PROGENITORS USING DIRECT REPROGRAMMING

RELATED APPLICATIONS

This application is a 35 U.S.C. § 371 filing of International Application No. PCT/KR2013/008888, filed Oct. 4, 2013, which claims priority to Korean Patent Application No. 10-2013-0091179, filed Jul. 31, 2013, each of which are incorporated herein by reference in their entireties.

TECHNICAL FIELD

The present invention relates to a method for preparing induced dopaminergic neuronal progenitors (iDPs) comprising inducing an expression of Oct4, Sox2, Klf4, and c-Myc genes in adult cells and direct reprogramming of the adult cells to the iDPs by treating the cells with sonic hedgehog (SHH) and fibroblast growth factor 8 (FGF8); and a cell therapy product and a composition for treating or preventing Parkinson's Disease (PD) which comprises the iDPs as active ingredients. In addition to this, the present invention relates to a method for preparing midbrain dopaminergic neurons comprising isolating NSC-like colony by culturing the iDPs, dissociating the isolated NSC-like colony, and culturing the cells on neural cell differentiation medium. Further, the present invention relates to a method for treating PD or a method for screening medicine for preventing or treating PD using the cells of the present invention.

BACKGROUND ART

A dopaminergic cell group is a crucial organization which is involved in movement control, hormone secretion control, and emotional control that are important in mammalian brains. Therefore, abnormalities in dopamine operability-mediated neuronal signaling cause various defects in nervous systems. For example, PD is a neurodegenerative disease of the extrapyramidal system, which is caused by specific degeneration of dopamine-producing neurons in substantia nigra. In terms of methods for treating PD, a method for orally administering 3,4-dihydroxyphenylalanine (i.e. levodopa) is generally carried out in order to supply reduced amount of produced dopamine, but sustainability of effects is known to be poor.

Recent methods for treating PD include an attempt to transplant midbrain ventral region of a 6 to 9 week-old aborted fetus including dopamine-producing neuronal progenitors in order to supply lost dopamine-producing neurons. However, at the current stage, this method has ethical and technical problems, such as requiring at least 5 to 10 fetal brain tissues for treating one patient, lacking effects on treatment in some cases, or causing side effects by overproduction of dopaminergic neural cells. Specifically, issues have been raised in various aspects, such as cell supply, ethical problems, danger of infection, contamination, immune rejection response to transplanted tissues, and low survival rate because of the fact that fetal tissues rely more on lipid metabolism than glycolysis.

In an attempt to solve problems regarding ethical aspects or supply shortage, for example, a method for using cerebral cortex, stria, and midbrain cells of pigs is suggested. The method requires complicated manipulations which change antigens on the cell surface (MHC class I antigen) to inhibit rejection response. For example, as far as methods for solving transplant rejection response are concerned, a method for locally inhibiting an immune response by transplanting Sertoli's cells at the same time is also suggested. It is possible to obtain cells for transplantation from relatives whose MHC is a match, bone marrow of others, a bone marrow bank, and a cord blood bank, but if patients' own cells can be used, the problem of rejection response can be solved without unnecessary manipulations. As such, using the dopaminergic neurons prepared in vitro from patients' own cells is considered to be promising.

Meanwhile, completely differentiated dopaminergic neurons have low settling rate in patients, and sustainable therapeutic effects are difficult to expect from the neurons. That is, reconstruction of brain function is required to treat injured neural tissues, and the cells, which have not been completely differentiated, and which may be differentiated specifically into the dopaminergic neurons in vivo, should be transplanted to form an appropriate link with surrounding cells (network formation). In the case where general neuronal stem cells are transplanted, there are not only ethical problems described above, but there are also problems involving possibility of differentiating transplanted stem cells into heterogeneous cell populations. Specifically, with respect to treatment for PD, it is required to selectively transplant the dopamine-producing neurons among the neurons containing catecholamine Up until now, cells for transplantation suggested to be used for treating PD are striatum, human fetal neuron-derived immortalized cell lines, human neurons produced after mitosis of NT2Z cells, primordial neural cells, the cells that are transfected by foreign genes to produce catecholamine such as dopamine, bone marrow stromal cells, ES cells in which the genes are manipulated, etc. In addition to this, it is also suggested to use the cells that express tyrosine hydroxylase by treating dopamine-producing neurons and NT2 neural cells with retinoic acid, wherein the dopamine-producing neurons and NT2 neural cells are formed by contacting fetal midbrain tissue-derived neural progenitors with FGF-8 and SHH. However, existing cells for transplantation have problems of heterogeneity because the ratio of dopamine-producing neurons or the ratio of the cells that are capable of being differentiated into the dopamine-producing neurons is not high within the existing cells for transplantation.

Specifically, among the methods above, one of the methods has been recently raised to solve immune rejection response by preparing patient-specific cells and to expect therapeutic effects via cell therapy by preparing necessary cells using pluripotent stem cells (embryonic stem cells or induced pluripotent stem cells). However, since the pluripotent stem cells can generally form teratoma, there is a danger of causing cancer when undifferentiated pluripotent stem cells are transplanted. Consequently, a reprogramming method called direct conversion (direct reprogramming or transdifferentiation) has been newly developed. Possibility of tumorigenesis in the induced pluripotent stem cells can be avoided because direct conversion to desired cells is possible without going through the induced pluripotent stem cell stage via direct conversion.

It has been reported that neural stem cells can be prepared by the direct conversion method at the current stage (refer to Kim, J. et al. Direct reprogramming of mouse fibroblasts to neural progenitors. Proc Natl Acad Sci USA, 2011) and the neural stem cells that are prepared in this manner are called the induced neural stem cells. The induced neural stem cells are predicted to be used for treatment and research on various neurological disorders.

At the current stage, one of the biggest problems of transplantation treatment for PD is that differentiation-inducing neural stem cells or neuronal progenitors are differentiated into numerous cell types because of low efficiency in differentiating into dopaminergic neurons. Considering safety of neural circuit formation, it is preferable to use the cells that can be differentiated into desired cell type at high rate. Therefore, it is preferable to transplant terminally differentiated dopaminergic neurons in order to prevent heterogeneity, but when considering cell survival and an ability to form an appropriate network in the transplanted position within the brain, it is preferable to use the neural progenitors having self-renewal ability. Accordingly, an increased therapeutic effect for treatment can be expected using the dopaminergic neural progenitors which have high efficiency in differentiating into the dopaminergic neurons.

DISCLOSURE OF INVENTION

Technical Problem

Under this background, to overcome the above-described problems, the present inventors have made extensive efforts to research reprogramming process of patients' own differentiated cells to the dopaminergic neuronal progenitors and specifically, a method for increasing conversion rate of the dopaminergic neuronal progenitors that are differentiated into the dopaminergic neurons, thereby completing the present invention.

Technical Solution

It is an object of the present invention to provide a method for preparing the induced dopaminergic neuronal progenitors (iDPs), comprising inducing an expression of one or more pluripotency factors in adult cells; and direct reprogramming of the adult cells to the iDPs by treating the cells with sonic hedgehog (SHH) and fibroblast growth factor 8 (FGF8).

It is another object of the present invention to provide a method for preparing midbrain dopaminergic neurons, comprising isolating NSC-like colony by culturing the iDPs of the present invention; and dissociating the isolated colony, and culturing the cells on the neural cell differentiation medium.

It is still another object of the present invention to provide a cell therapy product which comprises the iDPs prepared by the method of the present invention as active ingredients.

It is still another object of the present invention to provide a pharmaceutical composition for treating or preventing PD which comprises the iDPs of the present invention as active ingredients.

It is still another object of the present invention to provide a method for treating or preventing PD comprising transplanting the iDPs of the present invention to a subject.

It is still another object of the present invention to provide a method for screening medicine for preventing or treating PD comprising treating the iDPs or dopaminergic neurons of the present invention with a candidate substance of medicine for preventing or treating PD.

Advantageous Effects

The progenitors prepared by the method for preparing the iDPs of the present invention can be widely used in the known art since the progenitors have significantly higher efficiency in differentiating into the dopaminergic neurons compared to conventional methods, and lack side effects such as immunogenicity and ethical issues because patients' own somatic cells can be used.

TH$^+$ neurons express dopaminergic neuron markers (indicated in red), such as Nurr1, Foxa2, Pitx3, and Ent (scale bar=50 μm).

Figure 5:
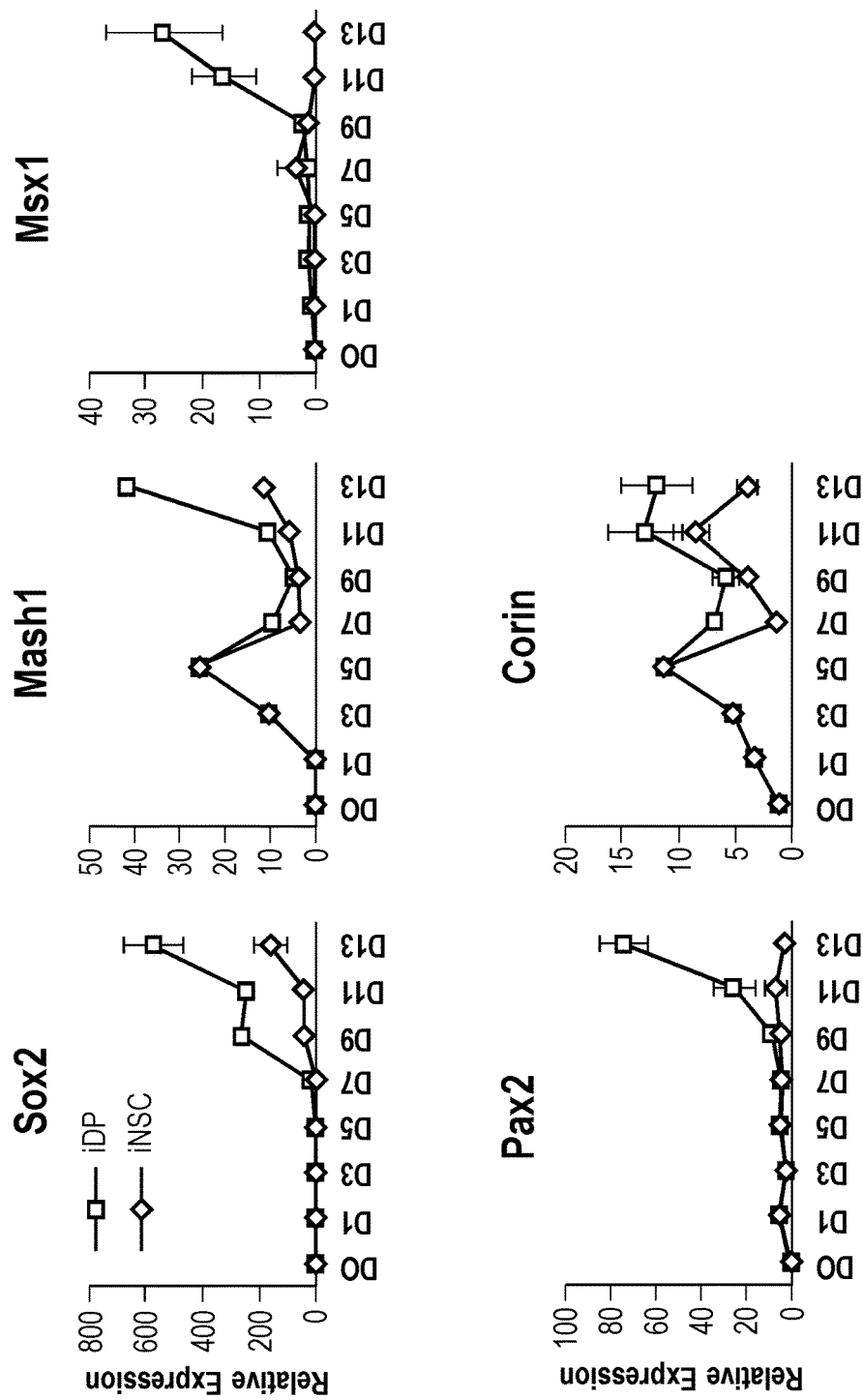

FIG. 5 is a diagram that analyzes a gene expression of neurons and midbrain dopaminergic neuronal progenitors markers during direct reprogramming to the iDPs. All the values are relative values for Day 0 (Mean±SE; n=3 to 5).

Figure 6:
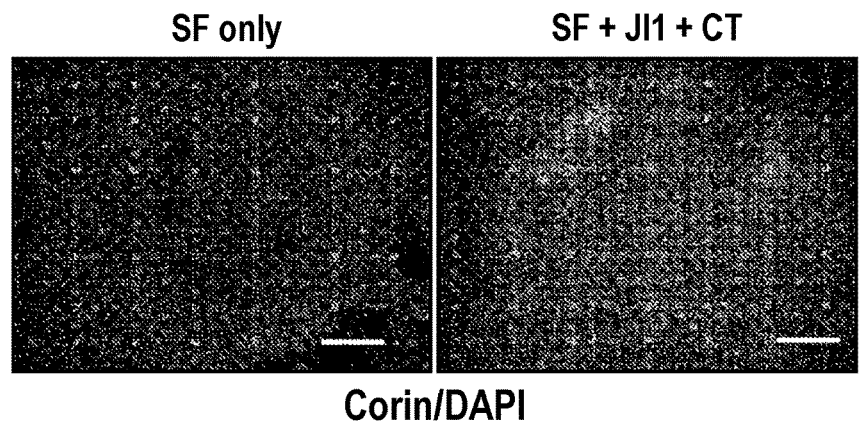

FIG. 6 is a diagram that shows the result of immunocytochemistry analysis on directly reprogrammed cells. The cells expressing Corin (indicated in red) can be detected and are present in high volume in the cells treated with JI1 and CT 99021 (scale bar=200 μm).

Figure 7:
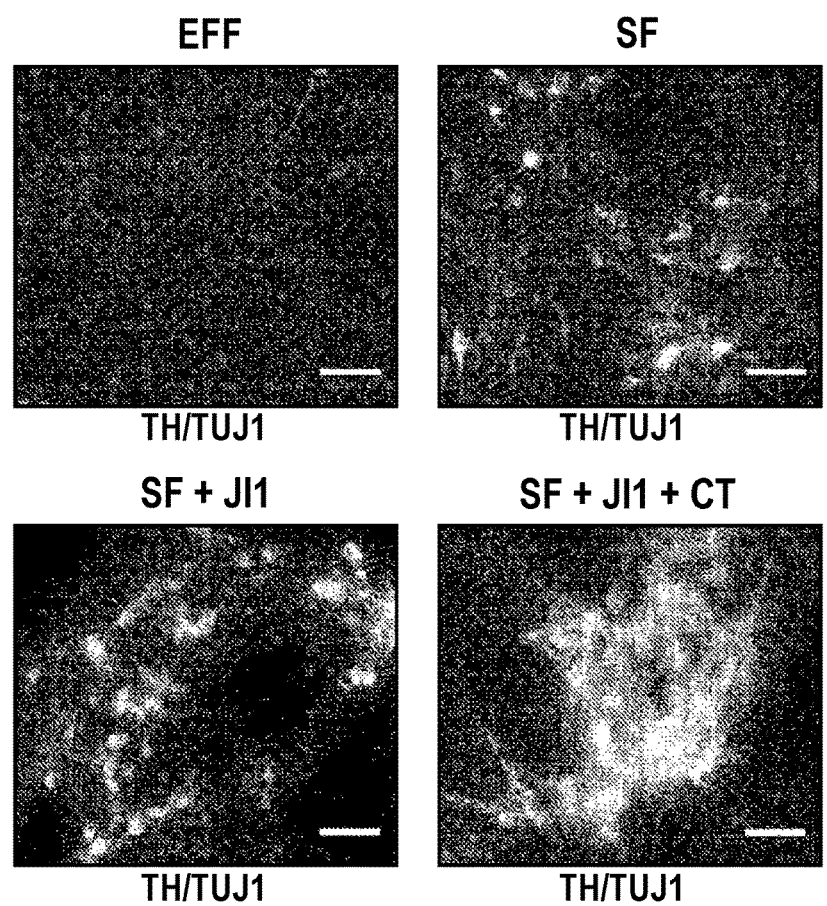

FIG. 7 is a diagram that shows the result of immunocytochemistry analysis on neurons that are positive to TH among the differentiated cells. The cells that are TH+ (indicated in green)/TUJ1+ (indicated in red) can be confirmed in the images showing the cells that were cultured under reprogramming conditions (scale bar=50 μm).

Figure 8A:
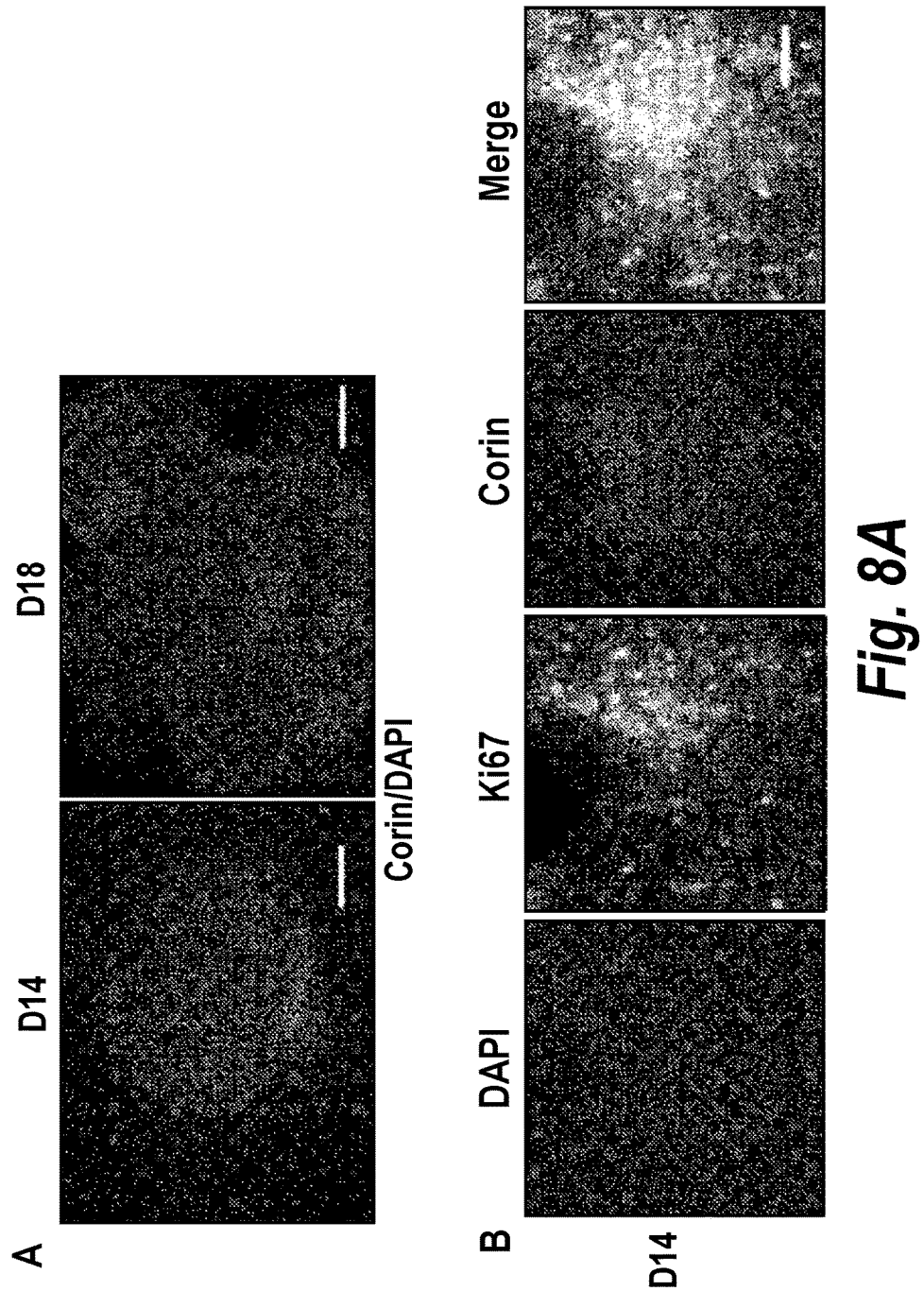

FIG. 8a is a diagram that shows the result analyzed by Corin (indicated in red) in the iDP colony which is isolated on Day 13 and cultured by the immunocytochemistry method. Corin-positive cells were increased in the culture medium including FGF2 on Day 18 (A of FIG. 8a). Further, it was confirmed that Corin (indicated in red) and Ki67 (indicated in green), which were markers of dividing cells, were co-stained (B of FIG. 8a) (A of FIG. 8a; scale bar=200 μm, B of FIG. 8a; scale bar=100 μm).

Figure 8B:
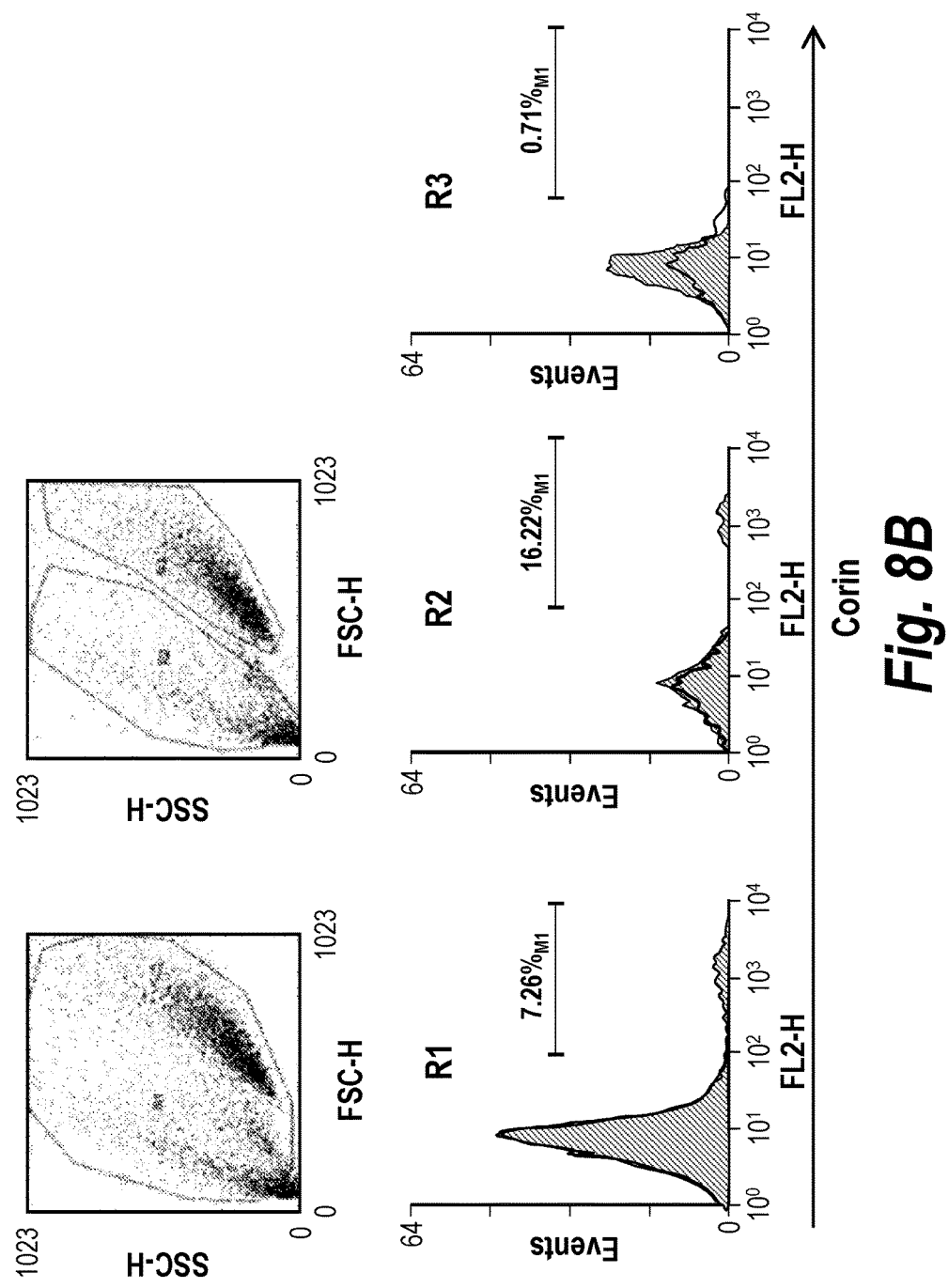

FIG. 8b shows that all of 7.26% of the cells express Corin on Day 18 from the result of flow cytometry analysis. The cell population expressing Corin can be isolated and present in high volume. Also, the cell population expressing Corin is included in the R2 group which account for 16.22%.

BEST MODE FOR CARRYING OUT THE INVENTION

In one aspect for achieving the above-described objects, the present invention provides a method for preparing the induced dopaminergic neuronal progenitors (iDPs) comprising: a) inducing an expression of one or more pluripotency factors in adult cells; and b) direct reprogramming of the adult cells to the iDPs by treating the cells of the step a) with sonic hedgehog (SHH) and fibroblast growth factor 8 (FGF8). The pluripotency factors may include Oct4, Sox2, Klf4, and c-Myc genes.

Specifically, the step a) may induce an expression of one or more pluripotency factors comprising Oct4 gene, and the pluripotency factors may include i) Oct4 gene, ii) Oct4 and Sox2 genes, iii) Oct4 and Klf4 genes, iv) Oct4 and c-Myc genes, v) Oct4, Sox2 and Klf4 genes, vi) Oct4, Sox2 and c-Myc genes, vii) Oct4, Klf4 and c-Myc genes, or viii) Oct4, Sox2, Klf4 and c-Myc genes.

As used herein, the term "direct reprogramming" refers to a technique for inducing direct conversion to desired somatic cells for direct cell treatment without producing the induced pluripotent stem cells through dedifferentiation process in order to solve problems including tumorigenesis occurring after cell transplantation because of remaining undifferentiated cells or low efficiency in differentiating into desired cells in the case where the induced pluripotent stem cells are prepared by reprogramming or de-differentiation from the existing adult cells and these induced pluripotent stem cells are induced to differentiate into desired specific cells. That is, in regard to the dedifferentiation of the adult cells, direct reprogramming refers to a method in which the adult cells are dedifferentiated into the cells which can differentiate into the desired cells, but not to the level of pluripotency, and they are directly differentiated to the target cells, thereby directly producing the desired cells. In the present invention, direct reprogramming can be used in combination with direct dedifferentiation, direct differentiation, direct conversion, direct transdifferentiation, and transdifferentiation. In the present invention, direct reprogramming may specifically refer to direct conversion to dopaminergic neural progenitors.

As used herein, the term "Dopaminergic Neuronal Progenitors (DPs)", which is a type of neural stem cells, is specifically a type of progenitors, wherein the efficiency in differentiating into the dopaminergic neurons is high and in vitro proliferation is possible. In the present invention, the DPs may be formed or prepared by an artificial method and specifically, the DPs may be the iDPs prepared by in vitro treatment.

As used herein, the term "adult cell", which refers to differentiated cells, represents the cells having completely or mostly lost multipotency which refers to an ability to differentiate into many types of cells. In the present invention, the adult cell may be the cells that are completely differentiated or may refer to the target cells that can recover partial multipotency or pluripotency by increasing an expression level of pluripotency factors. Specifically, the adult cell may be blood cells, liver cells, or fibroblasts.

In one embodiment of the present invention, the effects were confirmed by applying a method for preparing the iDPs of the present invention with regard to mouse embryonic fibroblasts (MEFs) and mouse tail tip fibroblasts (TTFs).

As used herein, the term "pluripotency factor" refers to the factors that have an important role for the stem cells to maintain stemness or for dedifferentiation in which the differentiated cells re-obtain stemness. That is, the term refers to the factors which make the cells to maintain or obtain self-renewal ability or multipotency. Specifically, the factors can function to reprogram the cells that are already being differentiated to pluripotent or multipotent cells again, and they may include OSKM factors, such as Oct4, Sox2, Klf4, and c-Myc (Yamanaka factors or OSKM factors), which are well known to be important for pluripotency. In the present invention, the pluripotency factor is the principle that includes dedifferentiation factors and can be used in combination with dedifferentiation factors.

After Dr. Yamanaka's team of Kyoto University in Japan disclosed that the overexpression of the Oct4, Sox2, Klf4, and c-Myc genes in mature somatic cells cause dedifferentiation which returns to an undifferentiated state similar to embryonic stem cells, the OSKM factors have been designated as dedifferentiated factors that make the differentiated cells to the undifferentiated state or the pluripotency factors that recover pluripotency. Sequences and information of the genes can be confirmed by the known database such as NCBI GenBank.

In the present invention, the term "a step of inducing a gene expression of pluripotency factors (Oct4, Sox2, Klf4, and c-Myc genes)" may be a method for increasing a gene expression level of pluripotency factors, specifically Oct4, Sox2, Klf4 and c-Myc genes, that are naturally present in cells, and may be a method for increasing a gene expression level of pluripotency factors in the cells by gene modification, expression vectors, introducing foreign expression gene, treatment using substance that has expression-inducing effect, etc. However, the term is not limited to any methods as long as the methods increase the expression level of pluripotency factors. Specifically, the term may be a method for inducing an expression under desired duration and conditions.

In the present invention, a step of increasing an expression level of pluripotency factors in differentiated cells may be carried out by the expression level or duration for re-obtaining multipotency that lead to the DPs. The duration may be at least 1 day or longer, and preferably 3 days or longer. However, as the step of increasing the expression level of the pluripotency factors becomes longer, the entire manufacturing period for the DPs also becomes longer, which may not be appropriate. Therefore, preferably, the period may last from 1 to 6 days, specifically from 3 to 6 days. However, the period is not limited as long as the reprogrammed cells reach the intermediate derivates state before obtaining pluripotency which has the same level as the embryonic stem cells.

In one embodiment of the present invention, OSKM factors, such as Oct4, Sox2, Klf4, and c-Myc (Yamanaka factors), were used as pluripotency factors. Specifically, transformed iPS cells, NGFP1 cells (Stemgent, USA), which can overexpress the OSKM factors when treated with Doxycyclin (Dox), are injected into blastocyst of C57BL/6 mouse and implanted in the surrogate mouse CD-1 (Harlan, USA), and then mouse embryonic fibroblasts (MEFs) are obtained from the fetus. When culturing the MEFs, the OSKM factors are overexpressed while the Dox is added in medium.

As used herein, the term "sonic hedgehog (SHH)" was initially discovered as a gene having an important role in fetal development, and specifically, the development of extremities, but SHH was not generally discovered in adult tissues. In the present invention, SHH may have been extracted, obtained largely by a recombinant technique or purchased commercially, but it is not limited to the source of origin.

As used herein, the term "fibroblast growth factor 8 (FGF8)", which is a type of a growth factor, induces proliferation by stimulating fibroblasts, and is known to have an important role in the development of fetal brain nerves. In the present invention, FGF8 may have been extracted, obtained largely by a recombinant technique or purchased commercially, but it is not limited to the source of origin.

In the present invention, the above step b), which is a step for preparing the DPs from the cells of the step a), may last from 6 to 10 days, and more preferably from 7 to 9 days. When the duration of the step b) is too short, efficiency in reprogramming into dopaminergic progenitors may be reduced, and if the duration is too long, the cells may directly differentiate into dopaminergic neurons instead of progenitors.

Meanwhile, the step b) may be treated with SHH at a concentration ranging from 100 to 400 ng/mL, and can be treated with FGF8 at a concentration ranging from 50 to 200 ng/mL, but it is not limited to the corresponding concentration as long as the iDPs with high differentiation efficiency into dopaminergic neurons of the present invention can be produced.

In one embodiment of the present invention, OSKM factor-expressing cells were cultured on RepM-DP culture medium containing 200 ng/mL of SHH (Peprotech, USA) and 100 ng/mL of FGF8b (Peprotech, USA) as inducing factors in advanced DMEM/F12 and neurobasal medium (1:1 mix) for 8 days. Meanwhile, reprogramming to neural stem cell (NSC) was induced as a control, and for this process, cells from Day 6 were cultured on RepM-DP culture medium containing 20 ng/mL of FGF2 (fibroblast growth factor 2), 2 ng/mL of FGF4 (fibroblast growth factor 4), and 20 ng/mL of EGF (epidermal growth factor) as inducing factors in advanced DMEM/F12 and neurobasal medium (1:1 mix) like above.

In addition, Jak-Stat signaling inhibitors and/or Wnt signaling agonists may be further treated in the step b). Specifically, Jak inhibitor, JI1; and one or more compounds selected from a group consisting of Wnt signaling agonists selected from a group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; a substance increasing β-catenin; GSK3β inhibitors such as lithium, LiCl, bivalent Zn, BIO, SB216763, SB415286, CHIR99021, QS11 hydrate, TWS119, kenpaullone, alsterpaullone, Indirubin-3'-oxime, TDZD-8, CT99021, or Ro 31-8220 methanesulfonate salt; Axin inhibitor, APC inhibitor, norrin, and R-spondin 2 may be further treated in the step b).

The Jak-Stat signaling inhibitors may be the Jak inhibitor 1 (JI1). However, conceptually, the Jak-Stat signaling inhibitors may also be the factors that inhibit important signaling for maintaining pluripotent cells or securing the pluripotency of the induced pluripotent stem cells. The Jak-Stat signaling of the Examples is included in the above-described signaling.

As used herein, the term "Wnt signaling agonist" refers to a substance which activates signaling in the Wnt signaling system, which controls various processes such as determination of cell fate, reconstitution of the structure, polarity, form, adhesion and growth, and maintenance and proliferation of undifferentiated cells during the embryonic development (refer to Logan & Nusse, Annu. Rev. Cell Dev. Biol., 2004; 20: 781-810). Herein, the Wnt signaling system does not have any limitations as long as Wnt-mediated signal or β-catenin-mediated signal can be delivered. Wnt signaling refers to a series of reactions that is initiated by the binding between Wnt, which is an initial substance causing Wnt signaling activation, and its receptors, or mediated by stabilization of beta-catenin (β-catenin), which is a downstream effective substance for Wnt signaling in the cells. Wnt signaling agonists are as following:

1) Direct addition of Wnt protein: Wnt, which is an initial substance causing Wnt signaling, is a secretory glycoprotein, and 19 types are known: Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16b are included.

2) Substances that increase β-catenin: Most cells react to Wnt signaling by an increase of β-catenin That is, an increase of non-phosphorylated form (or stabilized form) of β-catenin represents an increase of β-catenin in cytoplasm and an increase of β-catenin influx in cell nucleus.

3) Substances that phosphorylate Dishevelled or LRP tails, which is a co-receptor of Wnt:

4) Inhibitors of GSK3 (glycogen synthase kinase 3): lithium (Li), LiCl, bivalent Zn, BIO (6-bromoindirubin-3'-oxime), SB216763, SB415286, QS11 hydrate, TWS119, Kenpaullone, alsterpaullone, Indirubin-3'-oxime, TDZD-8, CT99021, and Ro 31-8220 methanesulfonate salt are included.

5) There are substances or RNAi that inhibit negative regulators of the Wnt signaling system, such as Axin and APC.

6) Protein that can activate Wnt signaling system, such as norrin and R-spondin2: Norrin binds to Frizzled 4-receptor, and R-spondin 2 react with Frizzled 8 and LRP6.

7) Gene transfer including transfection: Wnt-overexpressing composition or β-catenin overexpressing-composition may be used.

In one preferable aspect of the present invention, the Wnt signaling agonists are not limited to use substances that can activate Wnt signaling. However, preferably, the Wnt signaling agonists may be Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; a substance increasing β-catenin; GSK3β inhibitors such as lithium, LiCl, bivalent Zn, BIO, SB216763, SB415286, CHIR99021, QS11 hydrate, TWS119, kenpaullone, alsterpaullone, Indirubin-3'-oxime, TDZD-8, CT99021, or Ro 31-8220 methanesulfonate salt; Axin inhibitor, APC inhibitor, norrin, and R-spondin 2, and specifically CT99021.

In the present invention, Jak-Stat signaling inhibitors can eventually function to stimulate reprogramming to the DPs by inhibiting Jak-Stat signaling, which is important for reprogramming of self-renewal and pluripotency, and increasing the number of cells remaining as intermediate derivatives. Meanwhile, in the present invention, the Wnt signaling agonists can function to stimulate reprogramming to the midbrain dopaminergic neuronal progenitors.

The iDPs prepared by the method for preparing the iDPs of the present invention may express midbrain-specific markers, specifically including Ent, FoxA2, Pitx3, or Nurr1.

In one embodiment of the present invention, Jak-Stat signaling was inhibited by JI1 treatment, or Wnt signaling was activated by treating with CT99021 (CT), which is GSK3β-specific inhibitor. To determine the efficiency in differentiating into dopminergic cells, an expression of dopaminergic marker genes including En1, Lmx1a, Foxa2, and/or Corin was confirmed. As a result, it was confirmed that the ratio of the dopaminergic marker gene expression was significantly increased by the JI1 and/or CT treatment, and subsequently, production of the DPs was stimulated by the treatment.

In one aspect, the present invention provides a method for preparing midbrain dopaminergic neurons from the iDPs prepared by the method for preparing the iDPs of the present invention. Specifically, the present invention provides a method for preparing the midbrain dopaminergic neurons comprising isolating the NSC-like colony by culturing the iDPs, dissociating the isolated NSC-like colony, and culturing the cells on the neuronal cell differentiation medium.

As disclosed from above, the iDPs of the present invention, which are progenitors, form the NSC-like colony. Also, in spite of the fact that the iDPs of the present invention are the progenitors, they have property of expressing the midbrain markers. Therefore, when they are isolated and cultured on the neural cell differentiation medium, the efficiency in differentiating into the midbrain dopaminergic neurons is very high, thereby having an advantage that flexibility and heterogeneity (property of including many types of cells) as the neuronal progenitors are low, which is the purpose of the present invention. The method for differentiating from the iDPs to the midbrain dopaminergic neurons may be carried out by general methods of neural cell differentiation known in the field.

In one embodiment of the present invention, to determine the properties of the cells reprogrammed with SHH and FGF8, the dopaminergic neurons differentiated from the equal amount of both iDPs and induced neural stem cells were compared to each other under serum-free (SF) conditions, wherein the dopaminergic neurons differentiated from induced neural stem cells are used as a control. After 1 to 2 weeks of consecutive differentiation, it was confirmed that a ratio of $TH^+$ (tyrosine hydroxylase-positive)/$TUJ1^+$ (Neuron-specific class III β-tubulin-positive) dopaminergic neurons obtained from the reprogrammed iDPs (26.9±7.2%) was significantly higher than the ratio of the dopaminergic neurons obtained from the iNSCs (<3%). As such, it was shown that the ratio of the dopaminergic neurons became significantly higher when the neural cells were differentiated from the iDPs. It was determined that the dopaminergic neurons expressed midbrain-specific markers (En1, FoxA2, Pitx3, and Nurr1) by post-confirmation.

In one aspect, the present invention provides a cell therapy product, which comprises the iDPs prepared by the method as active ingredients, wherein the method comprises increasing an expression level of pluripotent factors in differentiated cells; and treating the cells with SHH and FGF8. The cell therapy product of the present invention may have effects on treating or preventing PD.

In another aspect, the present invention provides a method for preparing the cell therapy product.

In the present invention, the DPs, differentiated cells, pluripotent factors, SHH, and FGF8 are identical to the above explanation.

As used herein, the term "Parkinson's Disease (PD)" is a chronic and progressive neurodegenerative disease, which is caused by gradual loss of dopaminergic neurons dispersed in substantia nigra in the brain. It is predicted that the patients with PD account for about 1% of the population whose ages are 60 years old or over. Although the exact causes of PD are unknown, an established theory states that PD is a multifactorial disease encompassing genetic elements, elements caused by mutation, and defects in protein function. The causes have not been clearly defined, but it is common that symptoms finally occur due to the loss of dopaminergic neurons of the midbrain. Therefore, the disease is treated with strategies such as blocking the loss of the corresponding dopaminergic neurons, replacing the dopaminergic neurons, and relieving the conditions caused by the loss of the dopaminergic neurons (i.e. by levodopa).

As used herein, the term "cell therapy product", which refers to the cells and tissues prepared by isolation from an individual, culture, and specific manipulation, is pharmaceutical drug used for the purpose of treatment, diagnosis, and prevention (U.S. FDA regulation). The term also refers to the pharmaceutical drug used for the purpose of treatment, diagnosis, and prevention by a series of actions such as proliferating and selecting living autologous, allogenic, or xenogenic cells in vitro or changing biological properties of the cells by different methods in order to restore the function of cells or tissues.

As examined above, the iDPs prepared by the method of the present invention have higher differentiation efficiency than the method for differentiating from the existing neural stem cells because of significantly higher efficiency in differentiating into dopaminergic neurons, specifically into midbrain dopaminergic neurons. As neural progenitors, a desired amount of the iDPs can be proliferated in vitro, and an appropriate link (network formation) can be formed along with surrounding cells after the iDPs are transplanted into patients. Above all, the cells have an advantage that there are no technical problems such as immunogenicity and ethical problems since the patients' own somatic cells are used.

In one aspect, the present invention provides a pharmaceutical composition for treating or preventing for PD, which comprises the iDPs or the dopaminergic neurons of the present invention as active ingredients. Specifically, the iDPs may be included.

In another aspect, the present invention provides a method for preparing the composition.

As used herein, the term "prevention" refers to all the activities that inhibit PD or postpone occurrence of diseases by the transplantation of the cells.

As used herein, the term "treatment" refers to all the activities of which symptoms caused by PD become improved or beneficially changed by the transplantation of the cells. The symptoms caused by PD may generally include resting tremor, spasticity, bradykynesia, and postural instability, and there may also be accompanied clinical symptoms including symptoms of autonomic nervous system, neuropsychiatric symptoms, cognitive dysfunction, sleep disorder, pain, tiredness, and smell disturbance.

The pharmaceutical composition may include well-known or generally used substances in the field that are useful for storage, transplantation, or settlement of living cells of the present invention. That is, the pharmaceutical composition may include matrix or excipients that can be accepted physiologically into the cells as supplements. Types of matrix and/or excipients may be considered appropriate in the field based on intended administration routes. The pharmaceutical composition may also selectively include other appropriate excipients or active ingredients that are used together when treating the cells.

The pharmaceutical composition can be administered properly to a subject based on conventional methods, administration routes, and administration dosage used in the field according to its purpose or necessity. In terms of administration routes, for example, for local treatment, the composition may be administered based on appropriate methods including intra-lesional administration, if necessary. Further, appropriate administration dosage and the number of administration may be selected based on the known method in the field, and an appropriate number of the iDPs or dopaminergic neurons may be included. Specifically, $10^5$ to $10^7$ cells/administration may be carried out for the iDPs and $10^6$ to $10^9$ cells/administration may be carried out for the dopaminergic neurons.

In one aspect, the present invention provides the use for the iDPs or the dopaminergic neurons of the present invention for treating or preventing PD. Specifically, when preparing medicine for treating or preventing PD, the use for the iDPs or dopaminergic neurons of the present invention is provided. The above DPs may specifically include the iDPs.

In one aspect, the present invention provides a method for preventing or treating PD comprising administering or transplanting a medically effective amount of the iDPs or dopaminergic neurons of the present invention to a subject.

The iDPs, dopaminergic neurons or PD are identical to the above explanation.

As used herein, the term "medically effective amount" refers to an appropriate number of cells which is sufficient to show preventing or treating effects on PD when administering or transplanting cells of the present invention, and the amount may be selected based on the number of administration or transplantation. Specifically, $10^5$ to $10^7$ cells/administration may be carried out for the iDPs and $10^6$ to $10^9$ cells/administration may be carried out for the dopaminergic neurons.

As used herein, the term "subject" includes horses, dogs, cats, pigs, goats, rabbits, hamsters, monkeys, guinea pigs, rats, mice, lizards, snakes, sheep, cows, fish, and birds without any limitations, and refers to arbitrary animals (for example, humans).

In another aspect, the present invention provides a method for screening medicine for preventing or treating PD, which comprises treating the iDPs or dopaminergic neurons of the present invention with candidate substance of medicine for preventing or treating PD.

The iDPs, dopaminergic neurons or PD are identical to the above explanation.

As used herein, the term "candidate substance of medicine for preventing or treating PD" may be independent hexane, protein, other extracts, natural products, or compounds and the like, which is predicted to be the substance that has a possibility to prevent or treat PD based on conventional methods of selection, or randomly selected.

The method for screening medicine for preventing or treating PD of the present invention was designed from the method of comparing the iDPs or dopaminergic neurons of the present invention treated with the candidate substance with the control that was not treated with the candidate substance.

Specifically, the method includes determining the corresponding candidate substance as medicine for preventing or treating PD when a proliferative activity of the cells is increased, an activity of the cells is increased, or the cell survival rate with respect to various stresses is increased, compared to the control not treated with the candidate substances when the iDPs or dopaminergic neurons of the present invention are treated with the candidate substance of medicine for preventing or treating PD.

As used herein, the term "control", which refers to a group comprising the iDPs or dopaminergic neurons which are not treated with the candidate substance of medicine for preventing or treating PD, represents a group comprising the cells that are in parallel relationship with the group treated with the candidate substance.

The substance selected by such screening method can act as the leading compound during the development process of medicine for preventing or treating PD, and new medicine for preventing or treating PD may be developed by modifying and optimizing the leading compound.

MODE FOR CARRYING OUT THE INVENTION

Hereinafter, the present invention will be described in details with reference to the following Examples. However, these Examples are for illustrative purposes only, and the scope of the present invention is not limited to these Examples.

Meanwhile, the reagents with no source of origins in the Examples were all purchased at Invitrogen (www.invitrogen.com).

Example 1

Confirming Direct Reprogramming and Differentiation of Mouse Embryonic Fibroblasts (MEF) to Dopaminergic Neuronal Progenitors (DP)

Example 1-1

Direct Reprogramming of Mouse Embryonic Fibroblasts (MEF) to Dopaminergic Neuronal Progenitors (DP)

The MEFs, the target cells of direct reprogramming, were prepared as disclosed in the previous reference (refer to Kim, J. et al. Direct reprogramming of mouse fibroblasts to neural progenitors. Proc Natl Acad Sci USA 2011; 108: 7838-7843) when carrying out the method for direct reprogramming to the DPs of the present invention.

Specifically, NGFP1 (Stemgent, USA) cells, which were induced pluripotent stem cells (iPS), were injected into blastocyst of C57BL/6 mouse and implanted in a surrogate mother mouse CD-1 (Harlan, USA), wherein four types of pluripotent factors (Yamanaka factors or OSKM factors) including Oct4, Sox2, Klf4, and c-Myc were expressed in the cells when treated with Doxycycline (Dox). 12.5 to 13.5 days after the implantation, the embryo was isolated from the surrogate mouse, and visceral organs such as head, organs, spinal cord, and reproductive organs were eliminated; and the MEFs were cultured, treated with Puromycin, selected, and utilized.

The selected MEF cells were plated on Matrigel-coated culture dishes (BD Biosciences, USA) at a concentration of $2 \times 10^4$ cells/cm$^2$ in Dulbecco's modified Eagle's medium (DMEM) containing 10% fetal bovine serum (FBS), 1% nonessential amino acid (NEAA), and 1% Penicillin/Streptomycin (P/S).

Figure 1A:
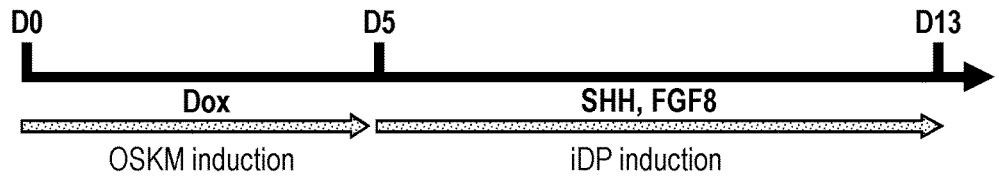
FIG. 1a is a synoptic diagram that shows direct reprogramming from reprogrammable mouse embryonic fibroblasts to the iDPs.

As disclosed in FIG. 1a, 1 day after cell seeding (D1), the cells were cultured in reprogramming initiation culture medium containing 10% knock-out serum replacer, 5% FBS, 1% NEAA, 2 mM GlutaMax (Invitrogen, USA), and 0.055 mM β-mercaptoethanol in knock-out DMEM for 4 days (until D5). Meanwhile, Dox inducing OSKM factors were included in the culture medium from D0 to D5.

5 days after cell seeding (D6), the cells were cultured in different culture medium to induce reprogramming to specific cells (DPs or neural stem cells).

Firstly, to induce reprogramming to the DPs, cells from Day 6 were cultured on RepM-DP culture medium comprising mixed medium of advanced DMEM/F12 and neurobasal medium (1:1 mix) containing 1×N2, 1×B27, 0.05% BSA, 2 mM GlutaMax and 0.11 mM β-mercaptoethanol; and 200 ng/mL SHH (Peprotech, USA), and 100 ng/mL FGF8b (Peprotech, USA) as inducing factors for the next 8 days. Meanwhile, reprogramming to neural stem cell (NSC) was induced as a control, and for this process, cells from Day 6 were cultured on RepM-DP culturing medium comprising the same mixed medium of advanced DMEM/F12 and neurobasal medium (1:1 mix); and 20 ng/mL FGF2 (fibroblast growth factor 2), 2 ng/mL FGF4 (fibroblast growth factor 4), and 20 ng/mL EGF (epidermal growth factor).

In regard to the cells that were cultured in different culture medium above, for neuronal cell differentiation, NSC-like colonies were selected and dissociated into single cells with Accutase (Millipore, www.millipore.com) and plated on poly-ornithine/laminin-coated culture dishes in neuronal cell differentiation medium comprising DMEM/F12 containing 1x×N2, 1×B27, 1.0 mM Glutamax, 0.11 mM β-mercaptoethanol, 1.0 mM dibutyryl-cAMP (Enzo, www.enzolifesciences.com), 0.2 mM ascorbic acid (Sigma), 10 ng/mL BDNF(brain-derived neurotrophic factor; Peprotech), and 10 ng/mL GDNF(glial cell line-derived neurotrophic factor; Peprotech). The medium was changed every 3 to 4 days.

Figure 1B:
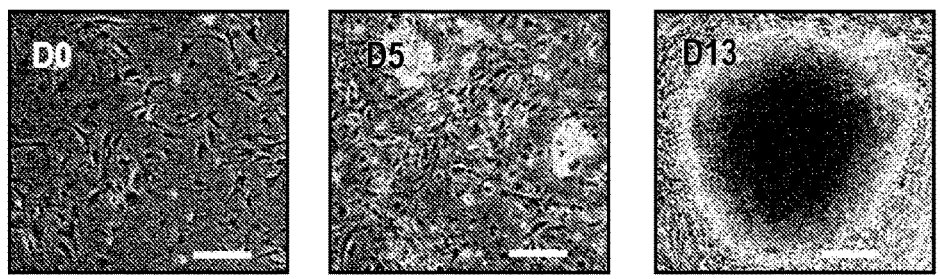
FIG. 1b is a diagram that shows a bright-field microscope image showing that a generation of NSC-like colony based on cell culture periods during the direct reprogramming to the iDPs (scale bar=100 μm).

As indicated above, SHH and FGF8 treatments were carried out for direct reprogramming to the midbrain DPs. 5 days after the induction of OSKM factors, the cells were further cultured under SHH- and FGF8-supplemented conditions (FIG. 1a). As a control, FGF2, EGF, and FGF4 were added to the culture medium for the generation of the iNSCs. It was confirmed that NSC-like colony was formed about 13 days after D0 when treated with SHH and FGF8 (FIG. 1b).

Example 1-2

Quantitative RT-PCR

Total RNA of cultured cells in Example 1-1 was extracted using Trizol solution (Invitrogen) from the cultured cells. Next, in regard to the total RNA, cDNA was synthesized from 1 μg of total RNA using the SuperScript III Reverse Transcriptase Kit (Invitrogen) and oligo (dT) primers (Invitrogen) according to the manufacturer's instructions. Quantitative RT-PCR was performed with Power SYBR Green Master Mix (Takara, www.takara.com) and analyzed using 7500 Fast Real-Time PCR system (Applied Biosystems, www.appliedbiosystems.com). The primers used are listed in Table 1 below.

TABLE 1

| Genes | Direction of Primers | Sequences (5'→3') |
|---|---|---|
| CORIN | Forward (SEQ ID NO: 1) | AGT GCC TCT CCT CGA GAT CC |
|  | Reverse (SEQ ID NO: 2) | CTC TCA AGA CCC TCT TTG GGG |
| EN1 | Forward (SEQ ID NO: 3) | CAA GAC TGA CTC ACA GCA ACC |
|  | Reverse (SEQ ID NO: 4) | ACT CCG CCT TGA GTC TCT GC |
| FOXA2 | Forward (SEQ ID NO: 5) | CTG GGA GCC GTG AAG ATG GA |
|  | Reverse (SEQ ID NO: 6) | ATT CCA GCG CCC ACA TAG GA |
| PAX2 | Forward (SEQ ID NO: 7) | GGC ATC TGD GAT AAT GAC ACA |
|  | Reverse (SEQ ID NO: 8) | GAT CCC GTT GAT GGA GTA GGA |
| MASH1 | Forward (SEQ ID NO: 9) | CCC TGA AAC TGG GTT GAT GT |
|  | Reverse (SEQ ID NO: 10) | AAA GGC TGT CCG AGA ACT GA |
| SOX2 | Forward (SEQ ID NO: 11) | TGC CTC TTT AAG ACT AGG GCT G |
|  | Reverse (SEQ ID NO: 12) | CGC CGC GAT TGT TGT GAT TA |
| LMX1A | Forward (SEQ ID NO: 13) | GGA CCA TAA GCG ACC CAA AC |
|  | Reverse (SEQ ID NO: 14) | CCT GAA CCA CAC GGA CAC TC |
| MSX1 | Forward (SEQ ID NO: 15) | GCC TCT CGG CCA TTT CTC AG |
|  | Reverse (SEQ ID NO: 16) | CGG TTG GTC TTG TGC TTG CG |

TABLE 1-continued

| Genes | Direction of Primers | Sequences (5'→3') |
|---|---|---|
| NGN2 | Forward (SEQ ID NO: 17) | GCT GTG GGA ATT TCA CCT GT |
|  | Reverse (SEQ ID NO: 18) | AAA TTT CCA CGC TTG CAT TC |
| GAPDH | Forward (SEQ ID NO: 19) | TGT TCC TAC CCC CAA TGT GT |
|  | Reverse (SEQ ID NO: 20) | TGT GAG GGA GAT GCT CAG TG |

Example 1-3

Immunocytochemistry

The cells cultured in Example 1-1 were immersed in 4% formaldehyde dissolved in PBS for 10 minutes and fixed, and washed with PBS four times. The fixed cells were blocked and permeabilized with Triton X-100, 10% FBS, and 1% BSA in PBS for 1 hour at room temperature. Next, after washing with PBS three times, the cells were incubated with primary antibody in blocking solution (PBS containing 10% FBS and 1% BSA) for 1 hour. The primary antibodies used are listed in Table 2 below. After the primary antibody reaction, the cells were washed with PBS three times and incubated for 1 hour at room temperature in PBS containing 1% BSA with anti-mouse Alexa 488-conjugated (1:500, Invitrogen), anti-mouse Alexa 546-conjugated (1:500, Invitrogen), anti-rabbit Alexa 488-conjugated (1:500, Invitrogen), or anti-rabbit Alexa 546-conjugated (1:500, Invitrogen) secondary antibodies. Fluorescent images were obtained using an Axio VertA.1 microscope (Carl Zeiss, www.zeiss.com).

TABLE 2

List of the used antibodies

| Target Proteins | Companies (cat. No.) | Dilution Ratio |
|---|---|---|
| TH | Sigma (T2928) | 1:1000 |
| TH | Millipore (AB152) | 1:1000 |
| TUJ1 | Covance (MMS-435P) | 1:500 |
| Nurr1 | Santa Cruz (sc-990) | 1:1000 |
| Pitx3 | Abcam (AB5722) | 1:200 |
| EN1 | DSHB (4G11-S) | 1:100 |
| Lmx1a | Millipore (AB10533) | 1:1000 |
| FoxA2 | Abcam (AB40874) | 1:1000 |
| Corin | Abnova (PAB12760) | 1:500 |
| Ki67 | BD (550609) | 1:200 |

Figure 1C:
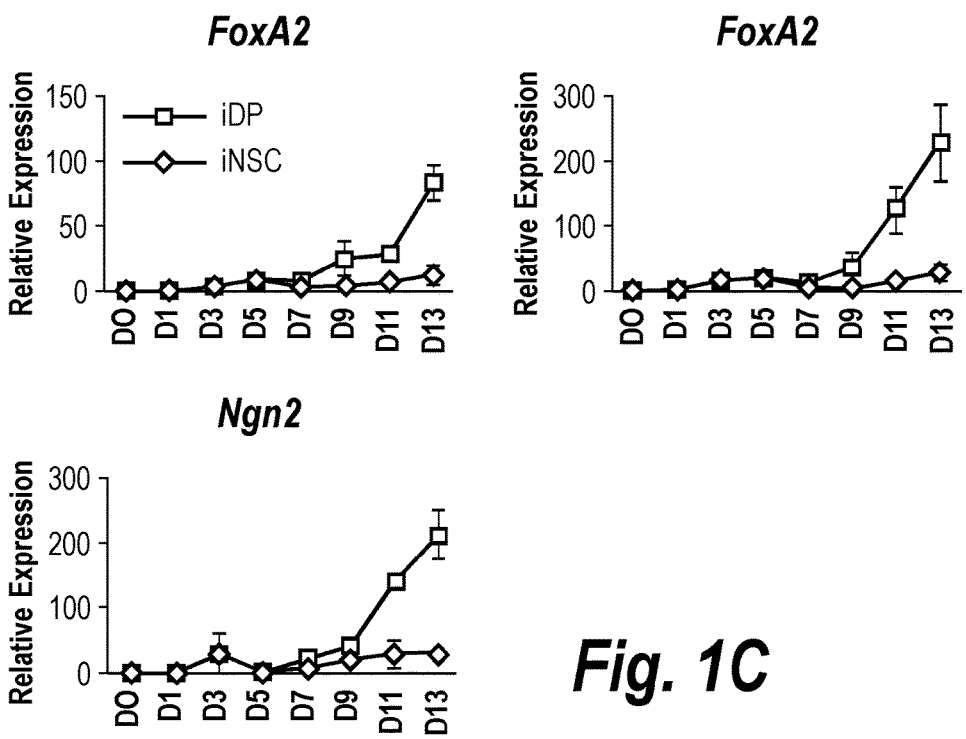
FIG. 1c is a graph that shows the result of gene expression analysis showing that important markers of midbrain dopaminergic neuronal progenitors (Foxa2, Lmx1a, and Ngn2) are differently expressed compared to direct reprogramming to the iNSCs during direct reprogramming to the dopaminergic neuronal progenitors.
Figure 1D:
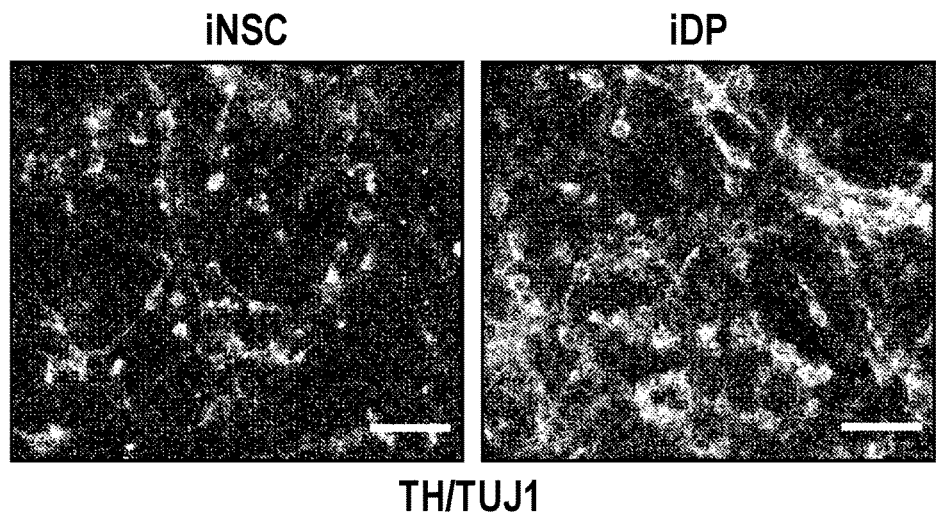
FIG. 1d is a diagram that shows the result of immunocytochemistry analysis on the terminally differentiated cells from the iNSCs and iDPs. The cells expressing TH (indicated in red), which is a marker of the dopaminergic neuronal progenitors, exist more in the differentiated cells from the iDPs. TUJ1, which is a maker of neurons, is indicated in green (scale bar=50 μm).
Figure 1E:
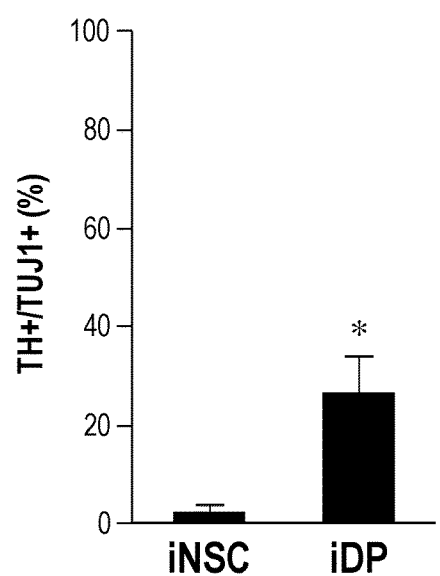
FIG. 1e is a graph that shows calculation of the percentage of TH-expressing neurons with respect to TUJ1-expressing neurons (Mean±SE, n=6, $p<0.01$).

When treated with SHH and FGF8, it was confirmed that NSC-like colonies were formed about 13 days after D0 (FIG. 1b), and marker genes of midbrain dopaminergic neuronal progenitors, such as Pax2, Lmx1a, Msx1, Ngn2, Foxa2, Sox2, and Corin, were detected 7 days after dox induction and 2 days after SHH and FGF8 supplementation (FIGS. 1c and 5). The results show that cell differentiation to the DPs can be specifically induced by the newly applied environmental factors, SHH and FGF8.

To determine the properties of the cells reprogrammed with SHH and FGF8, the dopaminergic neurons differentiated from equal amount of both the iDPs and iNSCs were compared to each other under serum-free (SF) conditions, wherein the dopaminergic neurons differentiated from the iNSC are used as a control. After 1 or 2 weeks of consecutive differentiation, it was confirmed that a ratio of $TH^+$ (tyrosine hydroxylase-positive)/$TUJ1^+$ (Neuron-specific class III β-tubulin-positive) dopaminergic neurons obtained from the reprogrammed iDPs (26.9±7.2%) was significantly higher than the ratio of the dopaminergic neurons obtained from the iNSCs (<3%).

These results show that the iDPs which have been reprogrammed with SHH and FGF8 have better ability to produce dopaminergic neurons compared to the iNSCs. Therefore, the iDPs with high producing potential for dopaminergic neurons could be obtained by pluripotency factor-mediated direct reprogramming (PDR) under SHH- and FGF8-supplemented conditions.

Example 2

Roles of Jak Inhibitors and Wnt Signaling Agonists During Direct Reprogramming to Dopaminergic Neuronal Progenitors (DP)

Although the cells could be reprogrammed to the iDPs, the efficiency in differentiating from the iDPs to $TH^+$ neurons was comparable to the efficiency in differentiating from the ESCs. Thus, to increase the efficiency in differentiating to the TH+ neurons in general, Jak-Stat signaling that could induce the differentiation to cardiomyocytes was initially inhibited using inhibitors of Jak-specific small molecules during the PDR process.

The experiment was carried out under the hypothesis that differentiation to the DPs are carried out by inhibiting Jak-Stat signaling which is important for self-renewal and reprogramming to pluripotency and by blocking other routes in which the pool of intermediate cells lead to the multipotent state.

Figure 2A:
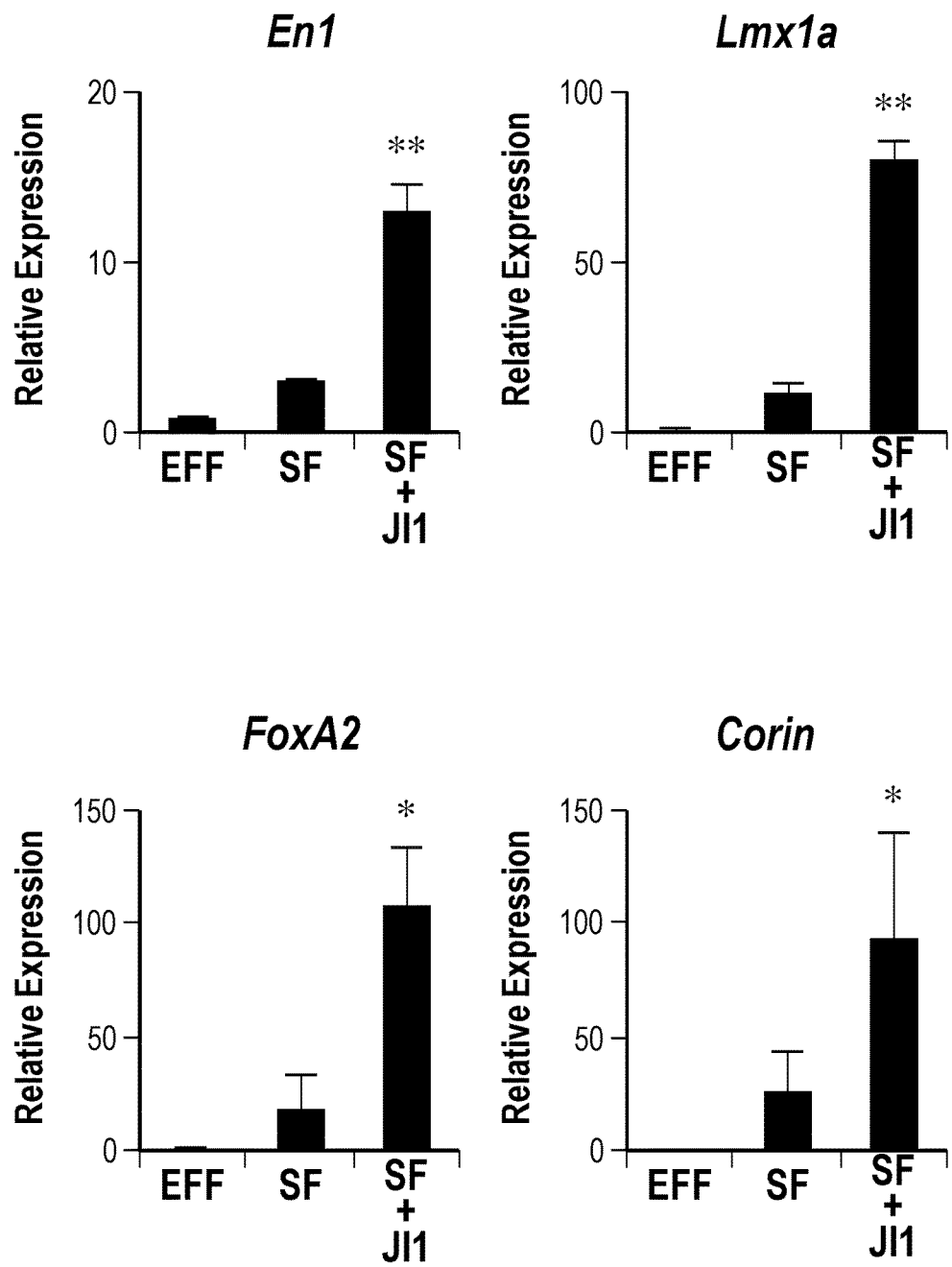
FIG. 2a is a diagram that shows the result of quantitative PCR analysis on dopaminergic markers that are increased by Jak inhibitor 1 (JI1) treatment. All the values on the diagram were indicated as relative expression values for an expression of the iNSCs which were treated with EGF. A statistical analysis was carried out using Student's t-test.
Figure 2B:
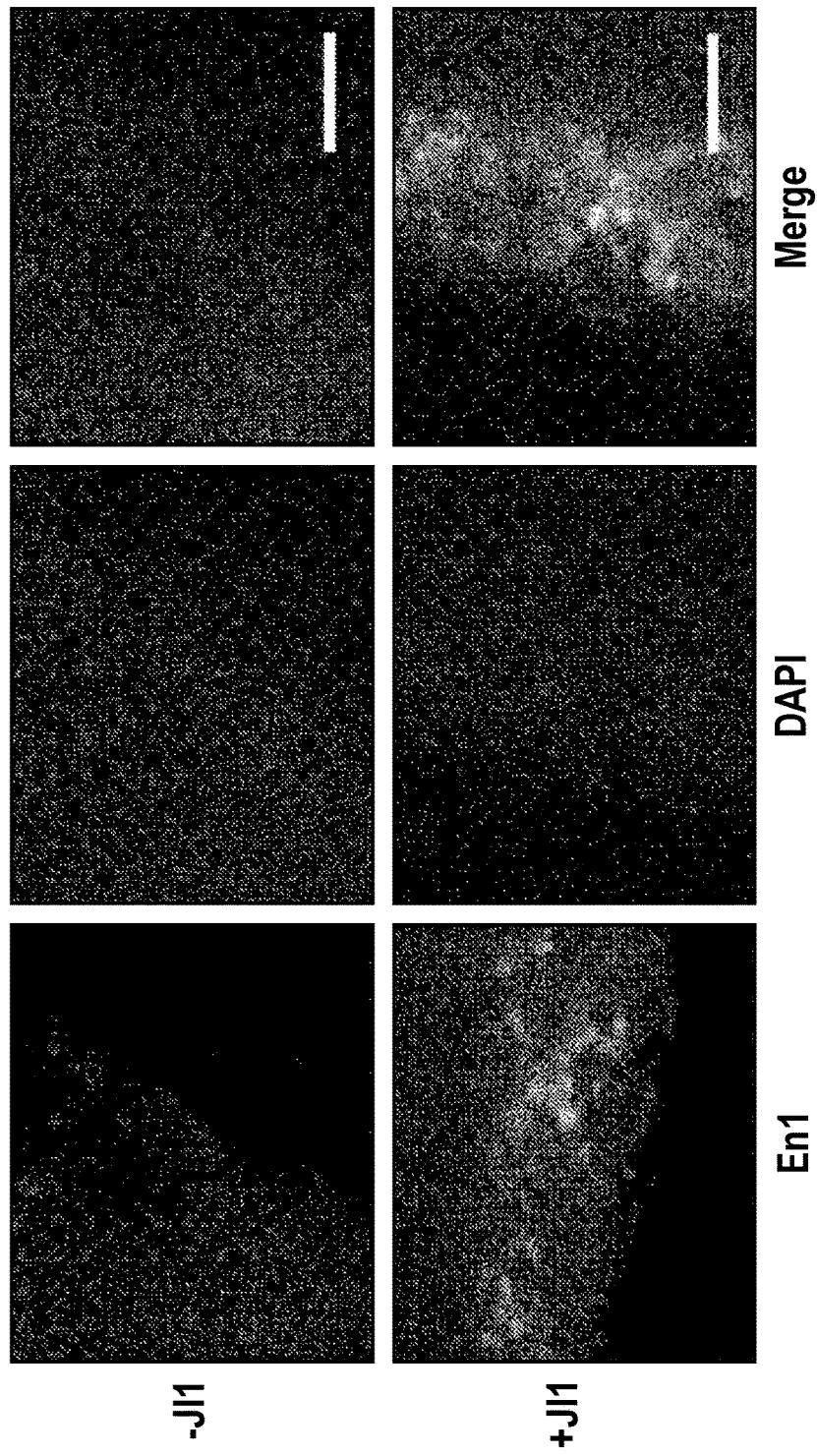
FIG. 2b is the result of immunocytochemistry analysis showing that En1, which is the midbrain dopaminergic marker, is increased in the culture medium treated with JI1 (scale bar=50 μm).

As expected from the experimental results above, when temporarily treated with the JI1 from Day 5 to Day 7, it was confirmed that the expression of dopaminergic marker genes, such as En1, Lmx1a, Foxa2, and Corin, was significantly increased compared to the untreated group (FIG. 2a), and it was also confirmed that En1-expressing cells were significantly increased in the JI1-treated iDP group using the immunocytochemistry method (FIG. 2b). Therefore, it was confirmed that the inhibition of Jak-Stat signaling for the cells in the intermediate stage was effective for the direct reprogramming to the DPs.

Figure 2C:
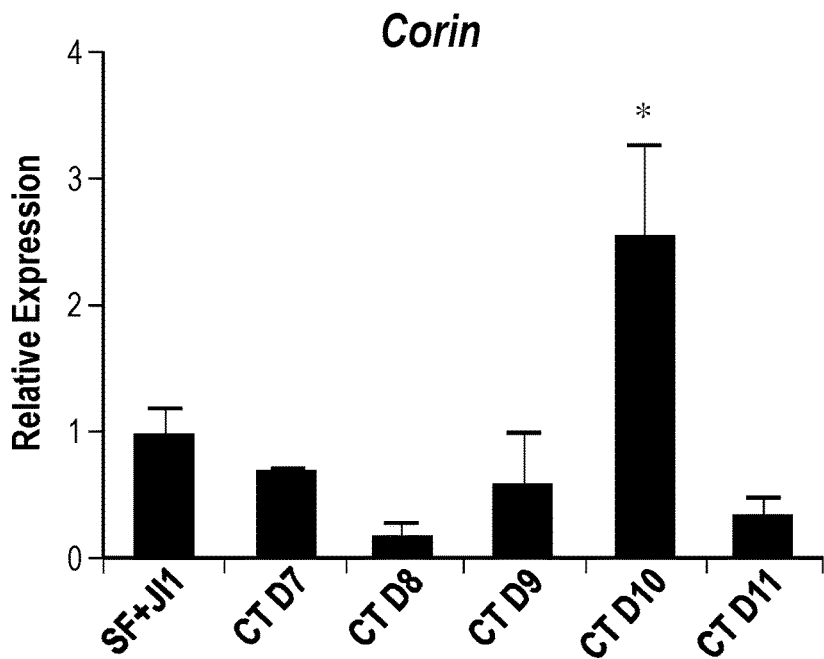
FIGS. 2c and 2d are diagrams that confirm optimal treatment duration and concentration of GSK3β inhibitor by measuring Corin expression, wherein Corin is a representative dopaminergic neuronal progenitor. The inhibitor was added since the experimentally designated date to Day 12. All the values were indicated as relative expression values with respect to a control (SF+JI1) which was not treated with CT. A statistical analysis was carried out using the Student's t-test (Mean±SE; n=3, $p<0.01(*)$, $p<0.001(**)$).
Figure 2D:
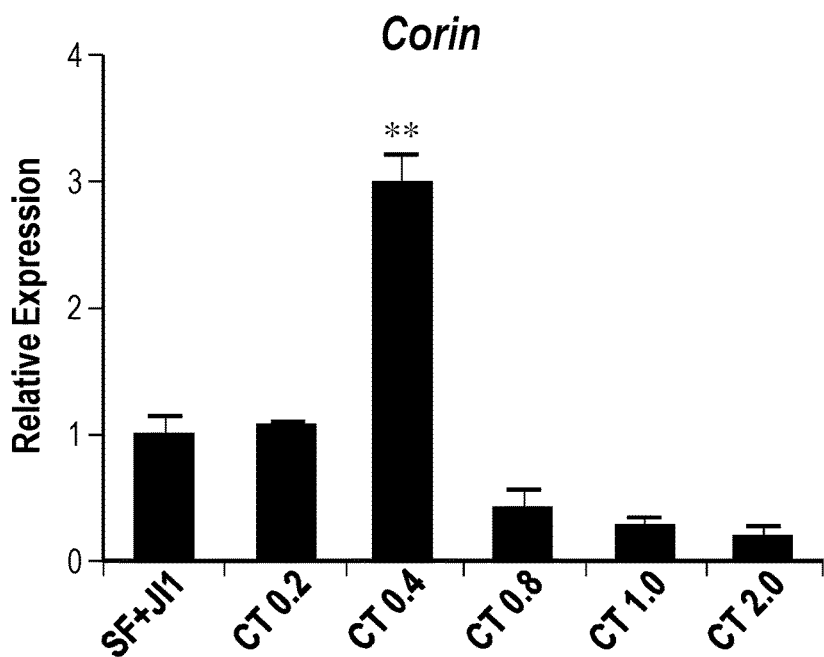

Next, Wnt signaling was considered, wherein the signaling was an important factor for midbrain dopaminergic neuron development in early (E9.5 to E10.5) and late (E11.5 to E12.5) stages and for differentiation of hESCs or iPSCs to dopaminergic neurons. To stimulate the iDP differentiation, Wnt signaling was activated by treating with CT99021 (CT) which was GSK3β-specific inhibitor, and the experiment was carried out to find an optimal treatment duration and treatment concentration of the CT. The level of differentiation was confirmed by an expression level of Corin protein, which was the main marker of the midbrain dopaminergic neurons (FIGS. 2c and 2d).

Figure 2E:
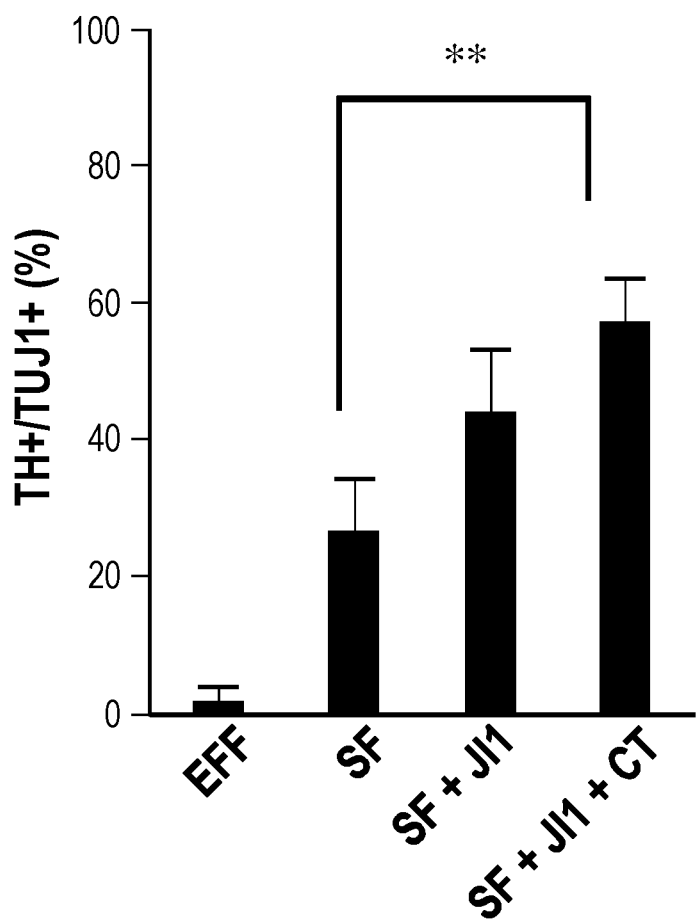
FIG. 2e is a graph that shows the value calculated from the percentage of $TH^+$ neurons among the entire neurons ($TUJ1^+$) that have been differentiated from the cells reprogrammed in various environment by immunocytochemistry analysis (Mean±SE; n=7 to 10, $p<0.001(**)$).

As the result of the experiment above, it was confirmed that differentiation to the dopaminergic neurons was stimulated when CT was treated under specific concentration and specific duration. On the other hand, Corin-expressing cells were only detected in the culture medium treated with the CT (FIG. 6). In addition to this, the combined treatment of CT and JI1 for the iDP development was also experimented (FIG. 2e). As a result, 44.3±8.4% of $TH^+/TUJ1^+$ neurons were produced when treated with JI1 alone, whereas 57.2±7.2% of $TH^+/TUJ1^+$ neurons were produced when treated with CT and JI1 together (FIG. 2e). Therefore, it was confirmed that the midbrain-specific process was significantly stimulated by the combined treatment of JI1 and GSK3β inhibitor during the PDR process of the present invention. Further, it was confirmed that the concentration and treatment duration of the CT should have been optimized to obtain the maximum reprogramming efficiency.

Figure 3A:
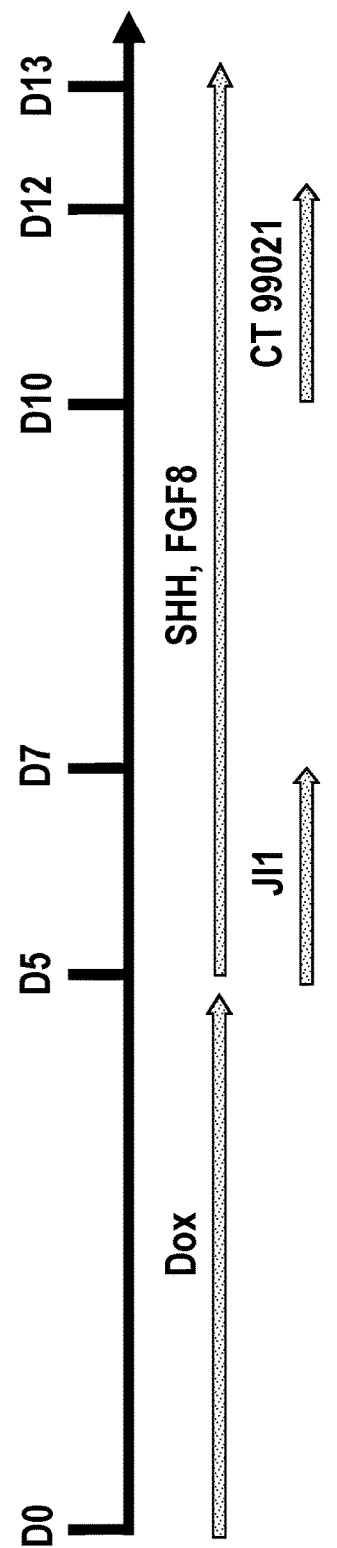
FIG. 3a is a synoptic diagram that shows an optimized protocol for direct reprogramming of the mouse fibroblasts to the iDPs.
Figure 3B:
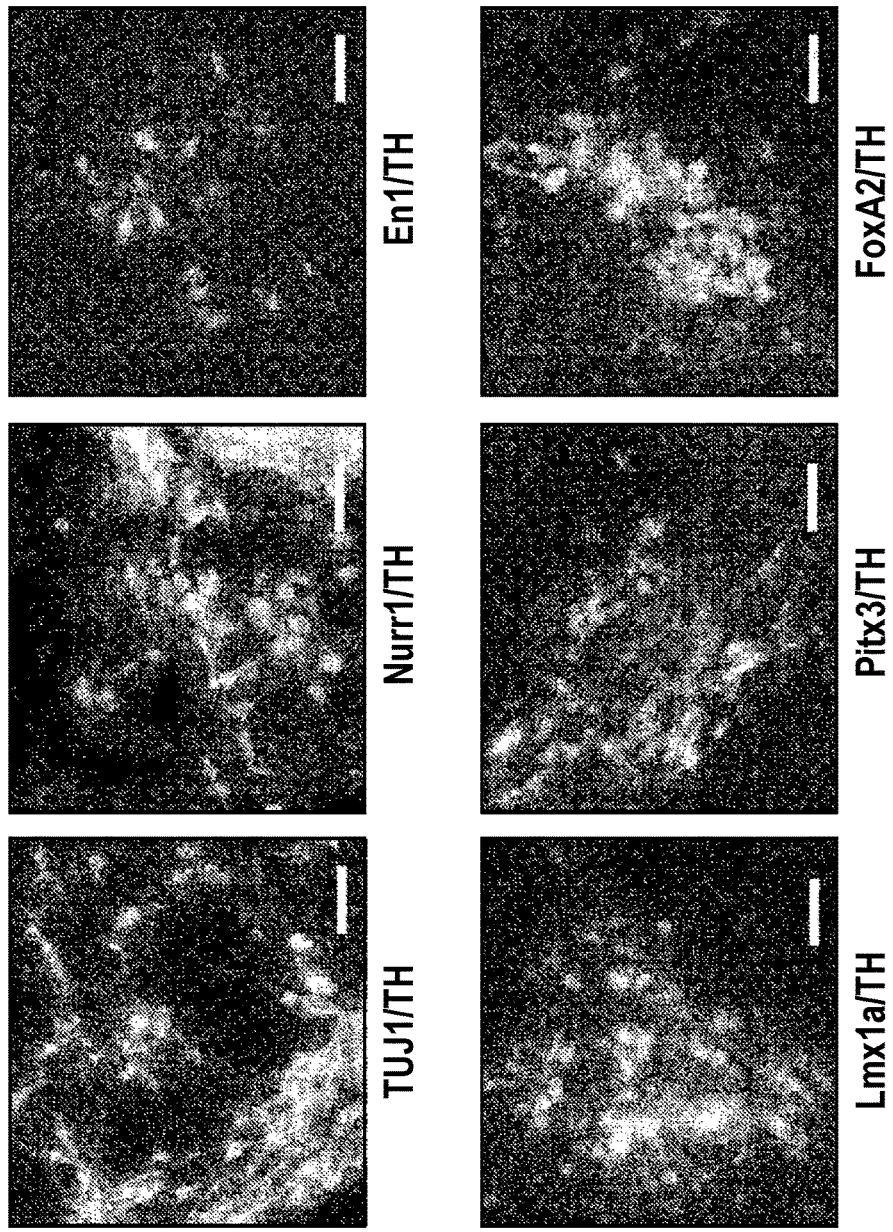
FIG. 3b is a diagram that shows an expression of the dopaminergic neuronal markers, such as TH, Nurr1, Pitx3, Lmx1A, and FoxA2, in neurons that have been differentiated from the iDPs treated with CT and JI1 by immunocytochemistry analysis.

After optimizing the iDP production process by the combined treatment of JI1 and CT (FIG. 3a), properties of the dopaminergic neurons differentiated from the iDPs were analyzed. It was confirmed that most TH+ dopaminergic neurons were co-stained for Nurr1, FoxA2, Lmx1a, Pitx3, and Ent (FIG. 3b), indicating that the differentiated dopminergic neurons of the present invention have some properties as the midbrain dopaminergic neurons, thus having potential of being used as cell therapy for PD. In addition to this, it was found that Corin-expressing iDPs could be self-renewed in vitro, and these cells could be effectively maintained by FGF2 treatment (FIGS. 8a and 8b).

Example 3

Measurement of Dopamine Using an Enzyme-linked Immunosorbent Assay 14 days after inducing the differentiation of the neuronal progenitors prepared in Examples 1 and 2 to dopaminergic neurons, an amount of the dopamine secretion in the differentiated cells was measured by conventionally known methods. Specifically, the cells were attached to a 24-well culture plate and washed with PBS. Next, the cells were treated with 200 μl of KCl solutions (low concentration: 4.5 mM/high concentration: 56 mM) in which the concentration was changed. Next, the amount of dopamine in the supernatants of each experimental group (a group treated with a low concentration of KCl/a group treated with a high concentration of KCl) was measured using an enzyme-linked immunosorbent assay kit (Rocky Mountain Diagnostics, Colorado, USA) according to the manufacturer's instructions (FIG. 3c).

Figure 3C:
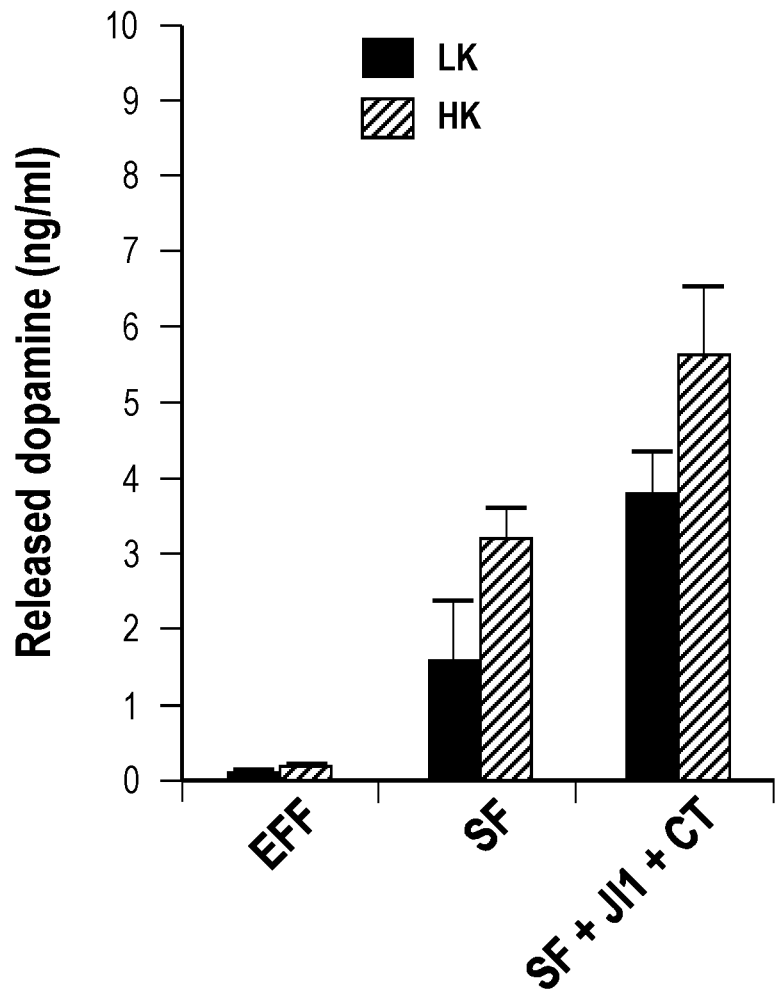
FIG. 3c is a diagram showing that dopamine secretion is significantly increased when treated with a high concentration of KCl (HK) compared to a low concentration of KCl (LK).
Figure 3D:
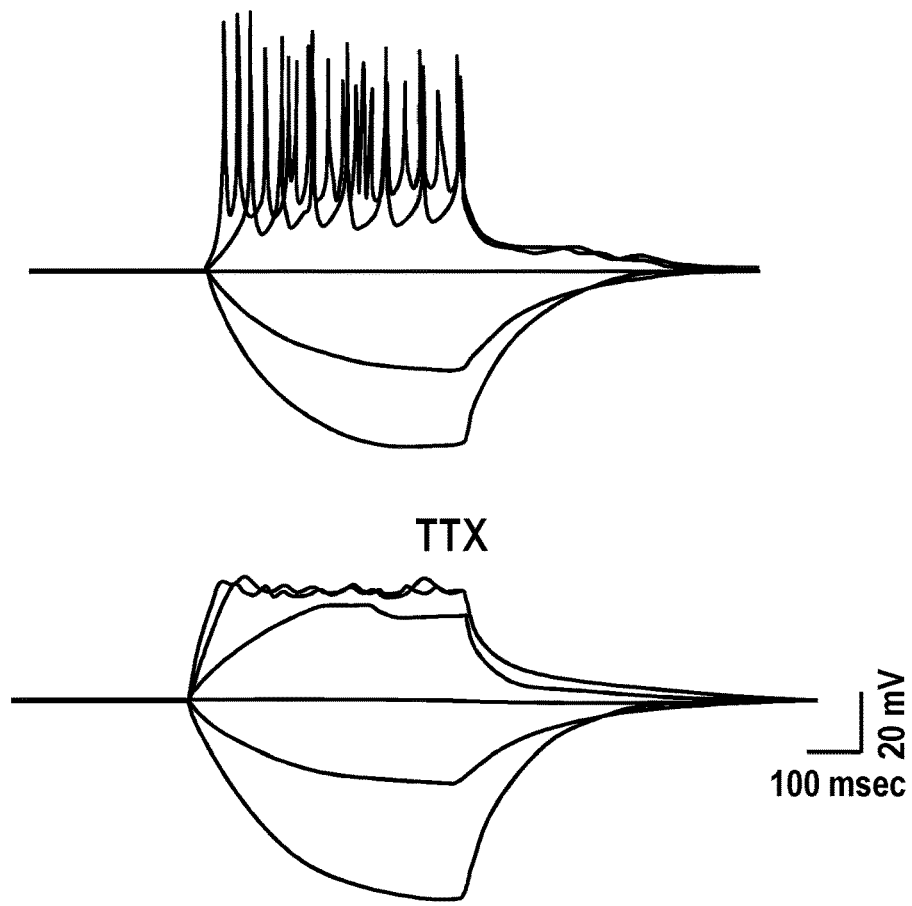
FIG. 3d is a representative diagram that measures membrane potential change and action potentials (APs) caused by a phased current injection method before and after tetrodotoxin (TTX) treatment.
Figure 3E:
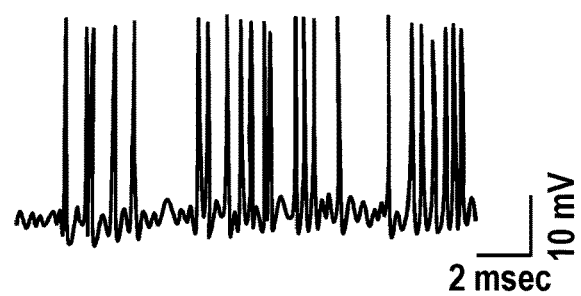
FIG. 3e is a diagram that measures voluntary APs shown in the cells of resting membrane potential.
Figure 3F:
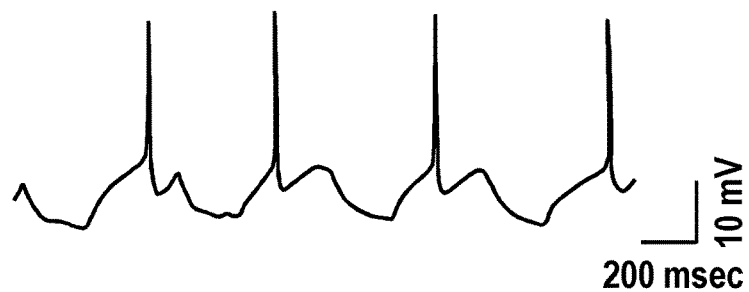
FIG. 3f is a diagram that measures rebound depolarization by membrane potential change of the cells.

As confirmed in FIG. 3C, dopamine secretion was significantly increased with high concentration of KCl (HK) as compared to low concentration of KCl (LK). From this, it was confirmed that the induction to the dopaminergic neurons was carried out effectively.

Example 4

Electrophysiological Test

An electrophysiological test using whole-cell patch clamp technique was carried out after terminally differentiating the DPs which were directly reprogrammed by the present invention to the neural cells. Specifically, continuously oxygenated (95% $O_2$, 5% $CO_2$) artificial cerebrospinal fluid (124 mM NaCl, 3.0 mM KCl, 1.23 mM $NaH_2PO_4$, 2.2 mM $CaCl_2$, 1.2 mM $MgCl_2$, 26 mM $NaHCO_3$, and 10 mM glucose, pH 7.4) went through perfusion after the cells were aliquoted on cover slip and moved to a recording underwater chamber. The whole-cell patch clamp record was measured at 31° C. while using glass pipette electrodes (3 to 5 MΩ) as patch electrodes.

To measure action potentials (APs), a glass pipette was filled with an inner solution (135 mM K-gluconate, 5 mM KCl, 2 mM $MgCl_2$, 5 mM EGTA, 10 mM HEPES, 0.5 mM $CaCl_2$, 5 mM Mg-ATP, and 0.3 mM Na-GTP) which was buffered with KOH having pH of 7.4. The resting membrane potential was predicted with the measured value that was measured immediately after breaking the membrane and forming whole-cell configuration for the experiment. APs were excited by a phased current injection method (10 pA per phase, current clamp mode, by 500 msec). Threshold, amplitude, half-width, and afterhyperpolarization (AHP) of initial APs were analyzed. Spontaneous firing was measured at current injection of 0 pA and rebound APs were induced by injecting hyperpolarized current of −20 pA. To block APs, 1 μM of tetrodotoxin (TTX) treatment was carried out. The patch-clamp record was obtained using MultiClamp 700B amplifier and Digidata1440 (Axon instruments). The obtained data was analyzed using pCLAMP version 10.2 (Axon instruments) and Mini-Analysis Program (Synaptosoft). From this, it was confirmed that the induction of the dopaminergic neurons was carried out effectively.

Example 5

Preparation of Lentivirus and Reprogramming of Mouse Tail Tip Fibroblasts (TTF)

Lentivirus was prepared in the same manner as the description in the previous reference (refer to Kim, J. et al. 2011). Specifically, $5×10^6$ 293 T cells were seeded on a 100 mm plate and cultured at 37° C. for 1 day. After culturing, the seeded 293T cells were transfected with 8 μg of pHAGE2-TetOminiCMV-STEMCCA or FUW-M2rtTA (Addgene, www.addgene.org) along with a packaging mixture (5 μg psPAX2 and 2.5 μg pMD2.G) (Addgene) and FuGENE HD transfection reagent (Promega, www.promega.com) according to the manufacturer's instructions. After culturing the transfected cells at 37° C. for 72 hours, they were filtered with a 0.45 μm filter prior to the use for preparing supernatants.

Meanwhile, the mouse TTFs were prepared in the same manner as the description in the previous reference (refer to Kim, J. et al. 2011). Specifically, mouse tail tissues were cut into small pieces (less than 0.5 cm) and cultured in the MEF culture medium on a gelatin-coated plate. Mouse TTFs were obtained after transferring the cells that moved out of the tissues onto a new plate and sub-culturing them.

The obtained cells were infected with virus expressing STEMCCA and rtTA, and were reprogrammed according to the procedure, in order to be used as the MEFs that can reprogram the cells.

Figure 4A:
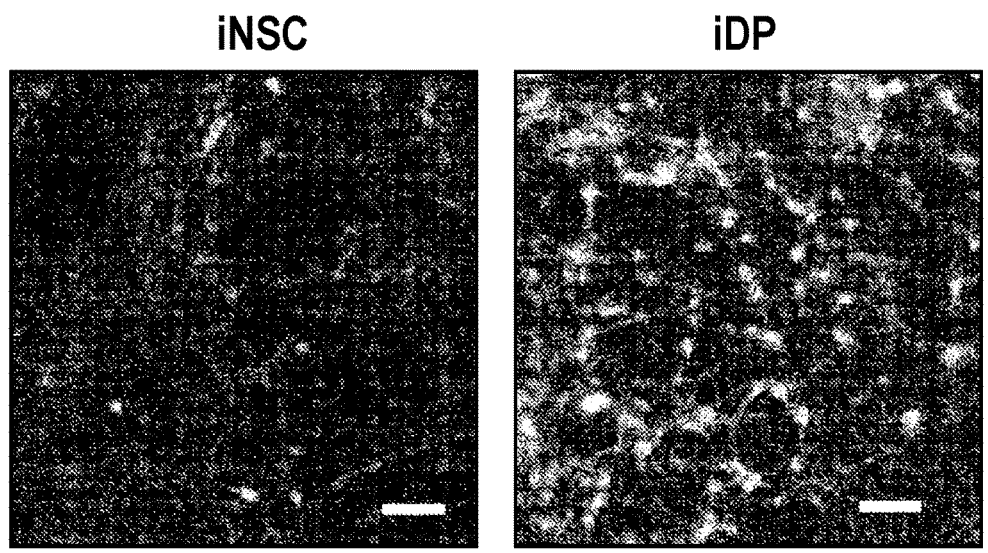
FIG. 4a is a diagram that shows an immunocytochemistry analysis on cells that are terminally differentiated from TTF-iNSCs or TTF-iDPs. The cells expressing TH (indicated in red), which is a marker of DPs exist more in the cells that are differentiated from TTF-iDPs (scale bar=50 μm).
Figure 4B:
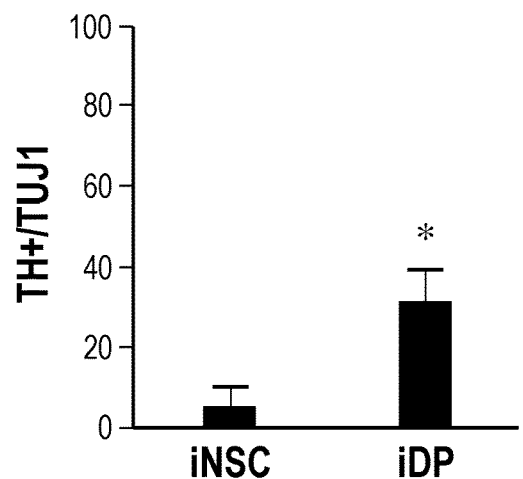
FIG. 4b is a diagram that shows the value obtained from the percentage of TH-expressing neurons with respect to the entire neurons (TUJ1$^+$), and the value is 31.7%±7.3%. The statistical analysis was carried out using the Student's t-test (Mean±SE, p<0.01(*)) (scale bar=50 μm).
Figure 4C:
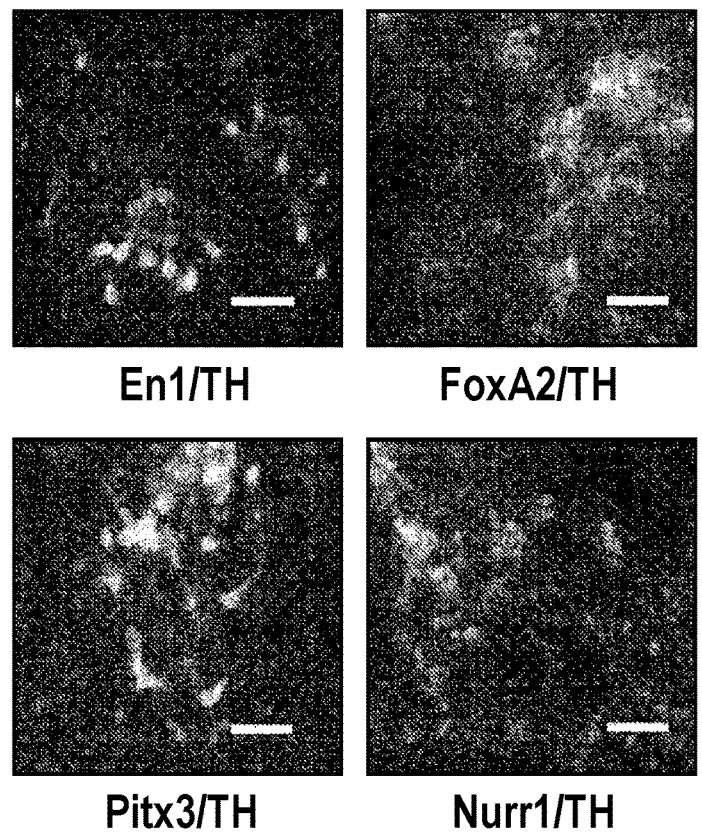

Finally, the efficiency in differentiation was measured by applying the direct reprogramming protocol leading towards the iDPs of the present invention from adult mouse TTFs using the STEMCCA system that can be induced by Dox of the present invention. Herein, as the result of observing the iDPs that were induced from the MEF, it was confirmed that the efficiency in differentiating into TH-expressing neurons was higher when being differentiated from TTF-iDP rather than from TTF-iNSC (FIGS. 4a and 4b). Further, it was confirmed that midbrain-specific markers including Ent, FoxA2, Pitx3, and Nurr1 were expressed in TH-expressing neurons (FIG. 4c). Therefore, it was confirmed that the adult mouse fibroblasts could be reprogrammed to the midbrain DP using the method of the present invention.

Example 6

Statistical Analysis

The results of lentivirus were shown as the mean±SE, and p values of 0.01 or 0.001 or less were evaluated as significant values in terms of statistical evaluation by carrying out the Student's unpaired t-test.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A method for preparing induced dopaminergic neuronal progenitors (iDPs) comprising: a) inducing expression of Oct4, Sox2, Klf4, and c-Myc genes in adult cells; and b) directly reprogramming the adult cell into iDPs by treating the adult cells of step a) with sonic hedgehog (SHH) and fibroblast growth factor 8 (FGF8), wherein the direct reprogramming occurs without producing induced pluripotent stem cells.

2. The method of claim 1, wherein the adult cells are blood cells, liver cells, or fibroblasts.

3. The method of claim 1, wherein the step a) occurs for 3 to 6 days.

4. The method of claim 1, wherein the step b) occurs for 6 to 10 days.

5. The method of claim 1, wherein SHH treatment is at a concentration ranging from 100 to 400 ng/mL and FGF8 treatment is at a concentration ranging from 50 to 200 ng/mL in the step b).

6. The method of claim 1, wherein the iDPs express midbrain-specific markers.

7. The method of claim 6, wherein the midbrain-specific markers comprise En1, FoxA2, Pitx3, or Nurr1.

8. A method of preparing midbrain dopaminergic neurons comprising: culturing the iDPs produced by the method according to claim 1 to form colonies of iDPs; isolating a colony of iDPs and dissociating the colony into single cells; and culturing the dissociated cells in a neuronal cell differentiated medium for a suitable amount of time to produce midbrain dopaminergic neurons.

9. A method for preparing induced dopaminergic neuronal progenitors (iDPs) comprising: a) inducing expression of Oct4, Sox2, Klf4, and c-Myc genes in adult cells; and b) directly reprogramming the adult cells into iDPs by treating the adult cells of step a) with sonic hedgehog (SHH) and fibroblast growth factor (FGF8), wherein the direct reprogramming occurs without producing induced pluripotent stem cells through a dedifferentiation process; and wherein the cells of step b) are further treated with a Jak inhibitor, and one or more compounds selected from the groups consisting of:

i) Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16b;

ii) a substance increasing β-catenin;

iii) GSK inhibitors selected from the group consisting of: lithium, LiCl, bivalent Zn, BIO, SB216763, SB415286, CHIR99021, and Ro 31-8220 methanesulfonate salt;

iv) an Axin inhibitor;

v) an APC inhibitor;

vi) a norrin inhibitor; and vii) R-spondin 2.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: CORIN rt-primer forward

<400> SEQUENCE: 1
agtgcctctc ctcgagatcc                                         20

<210> SEQ ID NO 2
<211> LENGTH: 21
<212> TYPE: DNA
<213> ORGANISM: Artificial Sequence
<220> FEATURE:
<223> OTHER INFORMATION: CORIN rt-primer reverse

<400> SEQUENCE: 2
ctctcaagac cctctttggg g                                       21

<210> SEQ ID NO 3
<211> LENGTH: 21
<212> TYPE: DNA
<213> ORGANISM: Artificial Sequence
<220> FEATURE:
<223> OTHER INFORMATION: EN1 rt-primer forward

<400> SEQUENCE: 3
caagactgac tcacagcaac c                                       21

<210> SEQ ID NO 4
<211> LENGTH: 20
<212> TYPE: DNA
<213> ORGANISM: Artificial Sequence
<220> FEATURE:
<223> OTHER INFORMATION: EN1 rt-primer reverse

<400> SEQUENCE: 4
actccgcctt gagtctctgc                                         20

<210> SEQ ID NO 5
<211> LENGTH: 20
<212> TYPE: DNA
<213> ORGANISM: Artificial Sequence
<220> FEATURE:
<223> OTHER INFORMATION: FOXA2 rt-primer forward

<400> SEQUENCE: 5
ctgggagccg tgaagatgga                                         20

<210> SEQ ID NO 6
<211> LENGTH: 20
<212> TYPE: DNA
<213> ORGANISM: Artificial Sequence
<220> FEATURE:
<223> OTHER INFORMATION: FOXA2 rt-primer reverse
```

```
<400> SEQUENCE: 6
attccagcgc ccacatagga                                                    20

<210> SEQ ID NO 7
<211> LENGTH: 21
<212> TYPE: DNA
<213> ORGANISM: Artificial Sequence
<220> FEATURE:
<223> OTHER INFORMATION: PAX2 rt-primer forward

<400> SEQUENCE: 7
ggcatctgdg ataatgacac a                                                  21

<210> SEQ ID NO 8
<211> LENGTH: 21
<212> TYPE: DNA
<213> ORGANISM: Artificial Sequence
<220> FEATURE:
<223> OTHER INFORMATION: PAX2 rt-primer reverse

<400> SEQUENCE: 8
gatcccgttg atggagtagg a                                                  21

<210> SEQ ID NO 9
<211> LENGTH: 20
<212> TYPE: DNA
<213> ORGANISM: Artificial Sequence
<220> FEATURE:
<223> OTHER INFORMATION: MASH1 rt-primer forward

<400> SEQUENCE: 9
ccctgaaact gggttgatgt                                                    20

<210> SEQ ID NO 10
<211> LENGTH: 20
<212> TYPE: DNA
<213> ORGANISM: Artificial Sequence
<220> FEATURE:
<223> OTHER INFORMATION: MASH1 rt-primer reverse

<400> SEQUENCE: 10
aaaggctgtc cgagaactga                                                    20

<210> SEQ ID NO 11
<211> LENGTH: 22
<212> TYPE: DNA
<213> ORGANISM: Artificial Sequence
<220> FEATURE:
<223> OTHER INFORMATION: SOX2 rt-primer forward

<400> SEQUENCE: 11
tgcctcttta agactagggc tg                                                 22

<210> SEQ ID NO 12
<211> LENGTH: 20
<212> TYPE: DNA
<213> ORGANISM: Artificial Sequence
<220> FEATURE:
<223> OTHER INFORMATION: SOX2 rt-primer reverse

<400> SEQUENCE: 12
cgccgcgatt gttgtgatta                                                    20

<210> SEQ ID NO 13
<211> LENGTH: 20
```

```
<212> TYPE: DNA
<213> ORGANISM: Artificial Sequence
<220> FEATURE:
<223> OTHER INFORMATION: LMX1A rt-primer forward

<400> SEQUENCE: 13
ggaccataag cgacccaaac                                              20

<210> SEQ ID NO 14
<211> LENGTH: 20
<212> TYPE: DNA
<213> ORGANISM: Artificial Sequence
<220> FEATURE:
<223> OTHER INFORMATION: LMX1A rt-primer reverse

<400> SEQUENCE: 14
cctgaaccac acggacactc                                              20

<210> SEQ ID NO 15
<211> LENGTH: 20
<212> TYPE: DNA
<213> ORGANISM: Artificial Sequence
<220> FEATURE:
<223> OTHER INFORMATION: MSX1 rt-primer forward

<400> SEQUENCE: 15
gcctctcggc catttctcag                                              20

<210> SEQ ID NO 16
<211> LENGTH: 20
<212> TYPE: DNA
<213> ORGANISM: Artificial Sequence
<220> FEATURE:
<223> OTHER INFORMATION: MSX1 rt-primer reverse

<400> SEQUENCE: 16
cggttggtct tgtgcttgcg                                              20

<210> SEQ ID NO 17
<211> LENGTH: 20
<212> TYPE: DNA
<213> ORGANISM: Artificial Sequence
<220> FEATURE:
<223> OTHER INFORMATION: NGN2 rt-primer forward

<400> SEQUENCE: 17
gctgtgggaa tttcacctgt                                              20

<210> SEQ ID NO 18
<211> LENGTH: 20
<212> TYPE: DNA
<213> ORGANISM: Artificial Sequence
<220> FEATURE:
<223> OTHER INFORMATION: NGN2 rt-primer reverse

<400> SEQUENCE: 18
aaatttccac gcttgcattc                                              20

<210> SEQ ID NO 19
<211> LENGTH: 20
<212> TYPE: DNA
<213> ORGANISM: Artificial Sequence
<220> FEATURE:
<223> OTHER INFORMATION: GAPDH rt-primer forward

<400> SEQUENCE: 19
```

```
tgttcctacc cccaatgtgt                                              20

<210> SEQ ID NO 20
<211> LENGTH: 20
<212> TYPE: DNA
<213> ORGANISM: Artificial Sequence
<220> FEATURE:
<223> OTHER INFORMATION: GAPDH rt-primer reverse

<400> SEQUENCE: 20
tgtgagggag atgctcagtg                                              20
```